(12) United States Patent
Kesten et al.

(10) Patent No.: US 10,463,242 B2
(45) Date of Patent: Nov. 5, 2019

(54) GUIDEWIRE NAVIGATION FOR SINUPLASTY

(71) Applicant: Acclarent, Inc., Menlo Park, CA (US)

(72) Inventors: Randy J. Kesten, Mountain View, CA (US); Rohit Girotra, Mountain View, CA (US)

(73) Assignee: Acclarent, Inc., Irvine, CA (US)

( * ) Notice: Subject to any disclaimer, the term of this patent is extended or adjusted under 35 U.S.C. 154(b) by 339 days.

(21) Appl. No.: 14/792,839

(22) Filed: Jul. 7, 2015

(65) Prior Publication Data

US 2016/0008083 A1   Jan. 14, 2016

Related U.S. Application Data

(60) Provisional application No. 62/022,607, filed on Jul. 9, 2014, provisional application No. 62/052,391, filed on Sep. 18, 2014.

(51) Int. Cl.
*A61B 1/233* (2006.01)
*A61B 17/24* (2006.01)
(Continued)

(52) U.S. Cl.
CPC .............. *A61B 1/233* (2013.01); *A61B 5/062* (2013.01); *A61B 5/6814* (2013.01);
(Continued)

(58) Field of Classification Search
CPC .. A61B 34/00; A61B 1/00; A61B 5/00; A61B 17/00; A61B 2034/00; A61B 2090/00; A61B 1/233
See application file for complete search history.

(56) References Cited

U.S. PATENT DOCUMENTS 5,967,980 A * 10/1999 Ferre ................. A61B 5/06
                                              600/424
6,016,439 A *  1/2000 Acker ................ A61B 5/06
                                              600/411
(Continued)

FOREIGN PATENT DOCUMENTS

CN       103118583 A    5/2013
CN       103298514 A    9/2013
(Continued)

OTHER PUBLICATIONS

Yamashita, Juli, et al. "Real-time 3-D model-based navigation system for endoscopic paranasal sinus surgery." IEEE Transactions on biomedical engineering 46.1 (1999): 107-116.*
(Continued)

*Primary Examiner* — Luther Behringer
*Assistant Examiner* — Sean D Mattson
(74) *Attorney, Agent, or Firm* — Frost Brown Todd LLC

(57) ABSTRACT

A method includes receiving image data, receiving surgical procedure data, and generating an operation plan. The image data is associated with anatomical structures in a nasal cavity of a patient. The image data and the surgical procedure data are received through a computing system. The act of generating an operation plan includes identifying a path for a surgical instrument in accordance with the image data and in accordance with the surgical procedure data. The act of generating the operation plan is performed through a computing system. The act of generating an operation plan further includes generating one or more instructional images depicting the identified path for the surgical instrument in a depiction of anatomical structures in the nasal cavity of the patient.

8 Claims, 16 Drawing Sheets

(51) Int. Cl.

| | | |
|---|---|---|
| *A61B 34/20* | (2016.01) | |
| *A61B 5/06* | (2006.01) | |
| *A61B 5/00* | (2006.01) | |
| A61B 6/00 | (2006.01) | |
| A61B 6/03 | (2006.01) | |
| A61B 34/00 | (2016.01) | |
| A61B 34/10 | (2016.01) | |
| A61B 5/055 | (2006.01) | |
| A61B 90/00 | (2016.01) | |
| A61B 90/14 | (2016.01) | |
| A61B 90/30 | (2016.01) | |

(52) U.S. Cl.
CPC .......... *A61B 5/6819* (2013.01); *A61B 5/6851* (2013.01); *A61B 17/24* (2013.01); *A61B 34/20* (2016.02); *A61B 5/055* (2013.01); *A61B 5/066* (2013.01); *A61B 5/4887* (2013.01); *A61B 5/743* (2013.01); *A61B 5/7425* (2013.01); *A61B 5/7435* (2013.01); *A61B 6/03* (2013.01); *A61B 6/501* (2013.01); *A61B 34/25* (2016.02); *A61B 90/14* (2016.02); *A61B 2034/107* (2016.02); *A61B 2034/2051* (2016.02); *A61B 2034/2072* (2016.02); *A61B 2090/306* (2016.02); *A61B 2090/365* (2016.02)

(56) References Cited

U.S. PATENT DOCUMENTS

| | | | | | |
|---|---|---|---|---|---|
| 6,151,404 | A | * | 11/2000 | Pieper | G06F 19/321 382/128 |
| 6,167,296 | A | * | 12/2000 | Shahidi | A61B 5/06 600/117 |
| 6,346,940 | B1 | * | 2/2002 | Fukunaga | G06T 15/20 345/420 |
| 7,072,501 | B2 | * | 7/2006 | Wood | A61B 6/032 382/132 |
| 7,167,180 | B1 | * | 1/2007 | Shibolet | G06T 7/155 345/418 |
| 7,720,521 | B2 | | 5/2010 | Chang et al. | |
| 7,822,461 | B2 | * | 10/2010 | Geiger | G06T 19/003 600/109 |
| 8,123,722 | B2 | | 2/2012 | Chang et al. | |
| 8,190,389 | B2 | | 5/2012 | Kim et al. | |
| 8,239,003 | B2 | | 8/2012 | Akins | |
| 8,320,711 | B2 | | 11/2012 | Altmann et al. | |
| 8,702,626 | B1 | | 4/2014 | Kim et al. | |
| 8,764,683 | B2 | | 7/2014 | Meller et al. | |
| 9,155,492 | B2 | | 10/2015 | Jenkins et al. | |
| 9,167,961 | B2 | | 10/2015 | Makower et al. | |
| 9,198,736 | B2 | | 12/2015 | Kim et al. | |
| 9,468,362 | B2 | | 10/2016 | Goldfarb et al. | |
| 2006/0004286 | A1 | * | 1/2006 | Chang | A61B 5/06 600/435 |
| 2007/0129751 | A1 | * | 6/2007 | Muni | A61B 17/24 606/196 |
| 2007/0208252 | A1 | * | 9/2007 | Makower | A61B 5/6851 600/424 |
| 2008/0183073 | A1 | * | 7/2008 | Higgins | G06T 19/003 600/425 |
| 2009/0297001 | A1 | * | 12/2009 | Markowitz | A61B 5/053 382/128 |
| 2010/0030031 | A1 | * | 2/2010 | Goldfarb | A61B 1/00066 600/163 |
| 2010/0241155 | A1 | * | 9/2010 | Chang | A61B 17/24 606/196 |
| 2011/0004057 | A1 | | 1/2011 | Goldfarb et al. | |
| 2011/0060214 | A1 | | 3/2011 | Makower | |
| 2012/0063644 | A1 | * | 3/2012 | Popovic | A61B 34/20 382/103 |
| 2012/0099778 | A1 | * | 4/2012 | Helm | A61B 6/4476 382/132 |
| 2014/0121676 | A1 | * | 5/2014 | Kostrzewski | A61B 19/26 606/130 |
| 2014/0200444 | A1 | | 7/2014 | Kim et al. | |
| 2014/0364725 | A1 | | 12/2014 | Makower | |
| 2016/0007842 | A1 | | 1/2016 | Govari et al. | |
| 2016/0183841 | A1 | * | 6/2016 | Duindam | A61B 17/34 600/424 |

FOREIGN PATENT DOCUMENTS

| | | | |
|---|---|---|---|
| EP | 1095628 | A2 | 5/2001 |
| WO | WO 2008/036050 | A2 | 3/2008 |
| WO | WO 2008/111070 | A2 | 9/2008 |
| WO | WO 2010/046802 | A1 | 4/2010 |
| WO | WO 2010/140074 | A1 | 12/2010 |
| WO | WO 2014/093880 | A1 | 6/2014 |

OTHER PUBLICATIONS

Bulu, Hakan, and Adil Alpkocak. "Comparison of 3D segmentation algorithms for medical imaging." Computer-Based Medical Systems, 2007. CBMS'07. Twentieth IEEE International Symposium on. IEEE, 2007.*
U.S. Appl. No. 14/792,823.
Bulli, H., et al., "Comparison of 3D Segmentation Algorithms for Medical Imaging," Twentieth IEEE International Symposium on Computer-Based Medical Systems, 2007 (CBMS '07), 6 pgs.
International Search Report and Written Opinion dated Oct. 8, 2015 for Application No. PCT/US2015/039501, 12 pgs.
International Search Report and Written Opinion dated Oct. 12, 2015 for Application No. PCT/US2015/039506, 13 pgs.
U.S. Appl. No. 62/022,607, filed Jul. 9, 2014.
U.S. Appl. No. 62/052,391, filed Sep. 18, 2014.
Australian Office Action dated Mar. 26, 2019 for Application No. 2015287957, 3 pages.
Australian Office Action dated Apr. 1, 2019 for Application No. 2015287961, 3 pages.
Chinese Office Action dated Mar. 15, 2018 for Application No. 201580037449.8, 14 pages.
Chinese Office Action dated Nov. 29, 2018 for Application No. 201580037449.8, 13 pages.
European Office Action dated Feb. 15, 2019 for Application No. 15747615.1, 7 pages.
U.S. Pat. Pub. No. 2016/0007842.

* cited by examiner

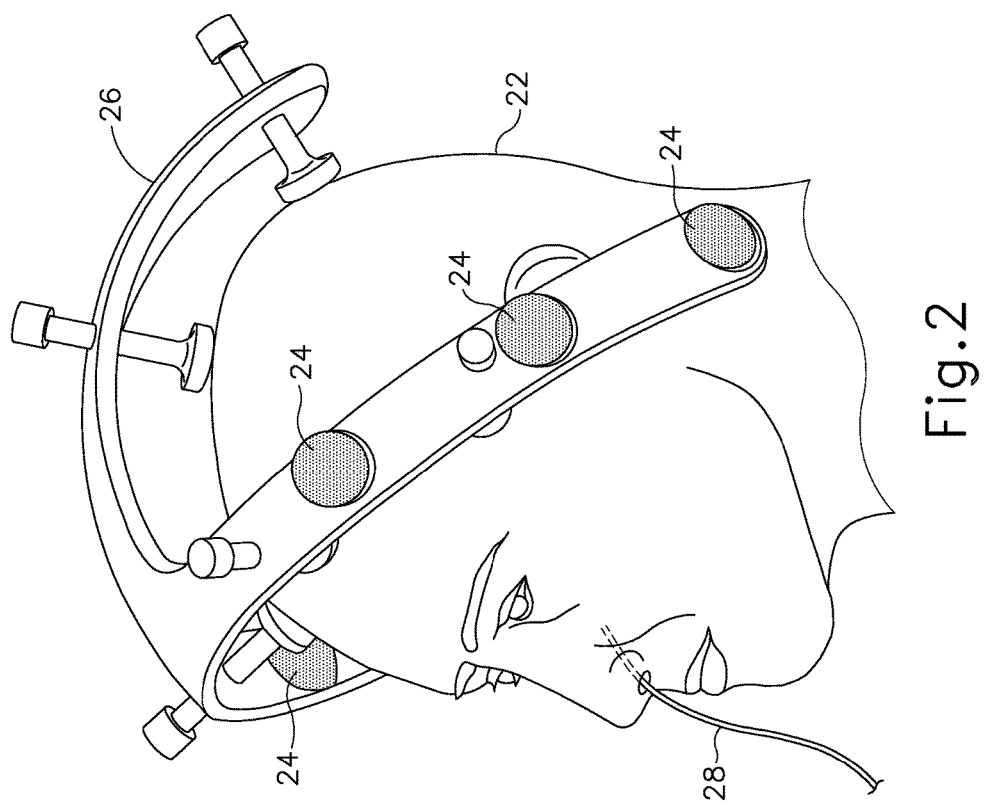

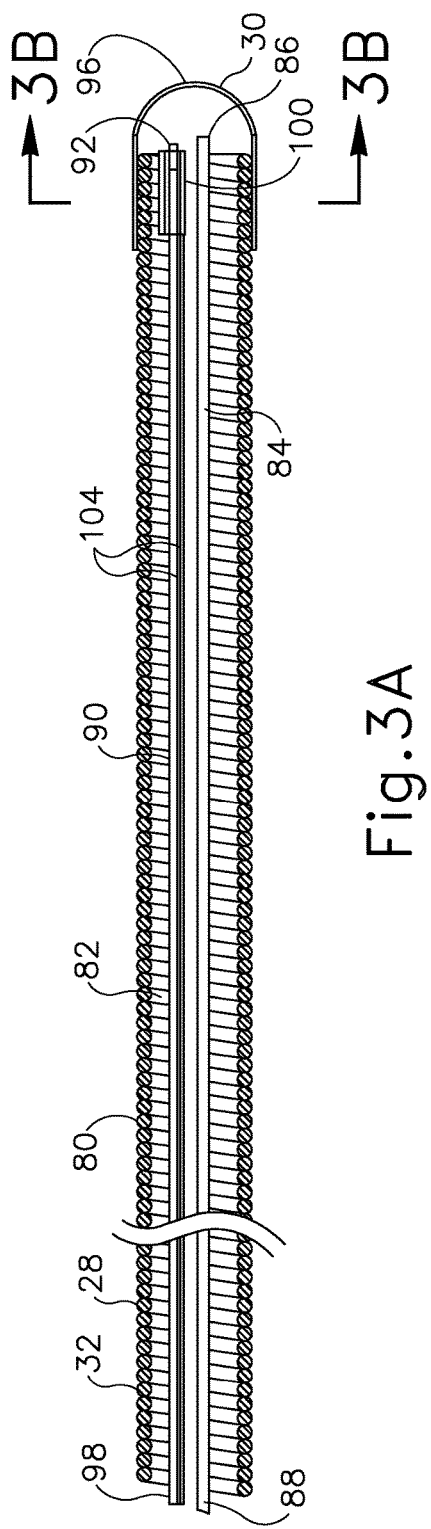
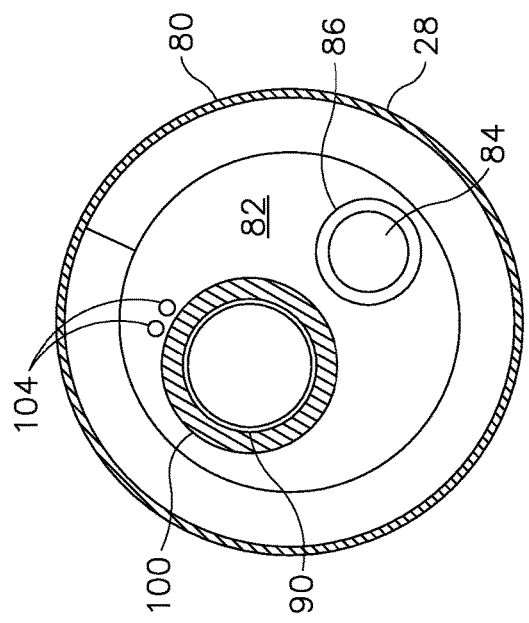
Fig.3A
Fig.3B

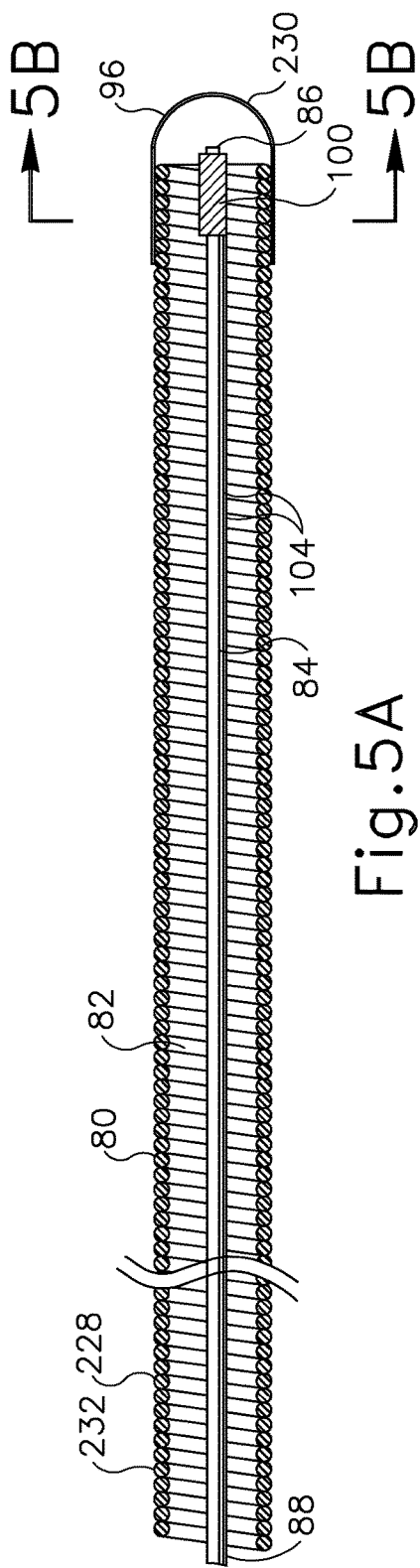
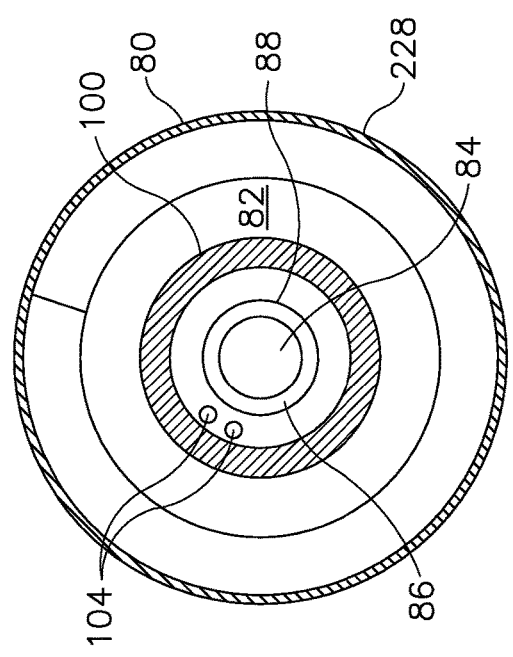
Fig.5A
Fig.5B

GUIDEWIRE NAVIGATION FOR SINUPLASTY

PRIORITY

This application claims priority to U.S. Provisional Patent App. No. 62/022,607, Jul. 9, 2014, entitled "Guidewire Navigation for Sinuplasty," the disclosure of which is incorporated by reference herein.

This application also claims priority to U.S. Provisional Patent App. No. 62/052,391, filed Sep. 18, 2014, entitled "Guidewire Navigation for Sinuplasty," the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Biosense Webster (Israel) Ltd. and Acclarent, Inc.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, three-dimensional map, etc.) so as to superimpose the current location of the instrument on the preoperatively obtained images. In some IGS procedures, a digital tomographic scan (e.g., CT or MRI, three-dimensional map, etc.) of the operative field is obtained prior to surgery. A specially programmed computer is then used to convert the digital tomographic scan data into a digital map or model. During surgery, instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map or model that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems and associated instruments that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

Other examples of IGS related methods, devices, and/or systems that may be modified for use in accordance with the teachings herein include but are not limited to those disclosed in U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Still further examples of IGS related methods, devices, and/or systems that may be modified for use in accordance with the teachings herein include but are not limited to those disclosed in U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. Pub. No. 2012/0245456, entitled "Adapter for Attaching Electromagnetic Image Guidance Components to a Medical Device," published Sep. 27, 2012, issued as U.S. Pat. No. 9,198,736 on Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. Pub. No. 2008/0281156, entitled "Methods and Apparatus for Treating Disorders of the Ear Nose and Throat," published Nov. 13, 2008, issued as U.S. Pat. No. 9,167,961 on Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

In some instances, it may be desirable to use IGS guidance when dilating an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used in conjunction with an IGS system during a dilation procedure to provide at least some degree of direct visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope and IGS system may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

When applied to functional endoscopic sinus surgery (FESS), balloon sinuplasty, and/or other ENT procedures, the use of an IGS allows the surgeon to achieve more precise movement and positioning of the surgical instruments than can be achieved by viewing through an endoscope alone. This is so because a typical endoscopic image is a spatially limited, two-dimensional, line-of-sight view. The use of an IGS provides a real time, three-dimensional view of all of the anatomy surrounding the operative field, not just that which is actually visible in the spatially limited, two-dimensional, direct line-of-sight endoscopic view. As a result, an IGS may be particularly useful during performance of FESS, balloon sinuplasty, and/or other ENT procedures, especially in cases where normal anatomical landmarks are not present or are difficult to visualize endoscopically.

In addition to simply providing visual feedback to the surgeon indicating the position of instruments within a patient, it may be desirable to use the equipment and software of an IGS system to provide detailed instructions to a surgeon. Such detailed instructions may be based on the unique anatomy of the particular patient, as mapped or modeled by the IGS system.

While several systems and methods have been made and used to perform ENT related surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a perspective view of the head of a patient, with components of the sinus surgery system of FIG. 1;

FIG. 3A depicts a cross-sectional side view of an exemplary guidewire that may be used with the sinus surgery system of FIG. 1;

FIG. 3B depicts a cross-sectional end view of the guidewire of FIG. 3A, taken along line 3B-3B of FIG. 3A;

FIG. 5A depicts a cross-sectional side view of another exemplary guidewire that may be used with the sinus surgery system of FIG. 1;

FIG. 5B depicts a cross-sectional end view of the guidewire of FIG. 5A, taken along line 5B-5B of FIG. 5A;

Figure 1:
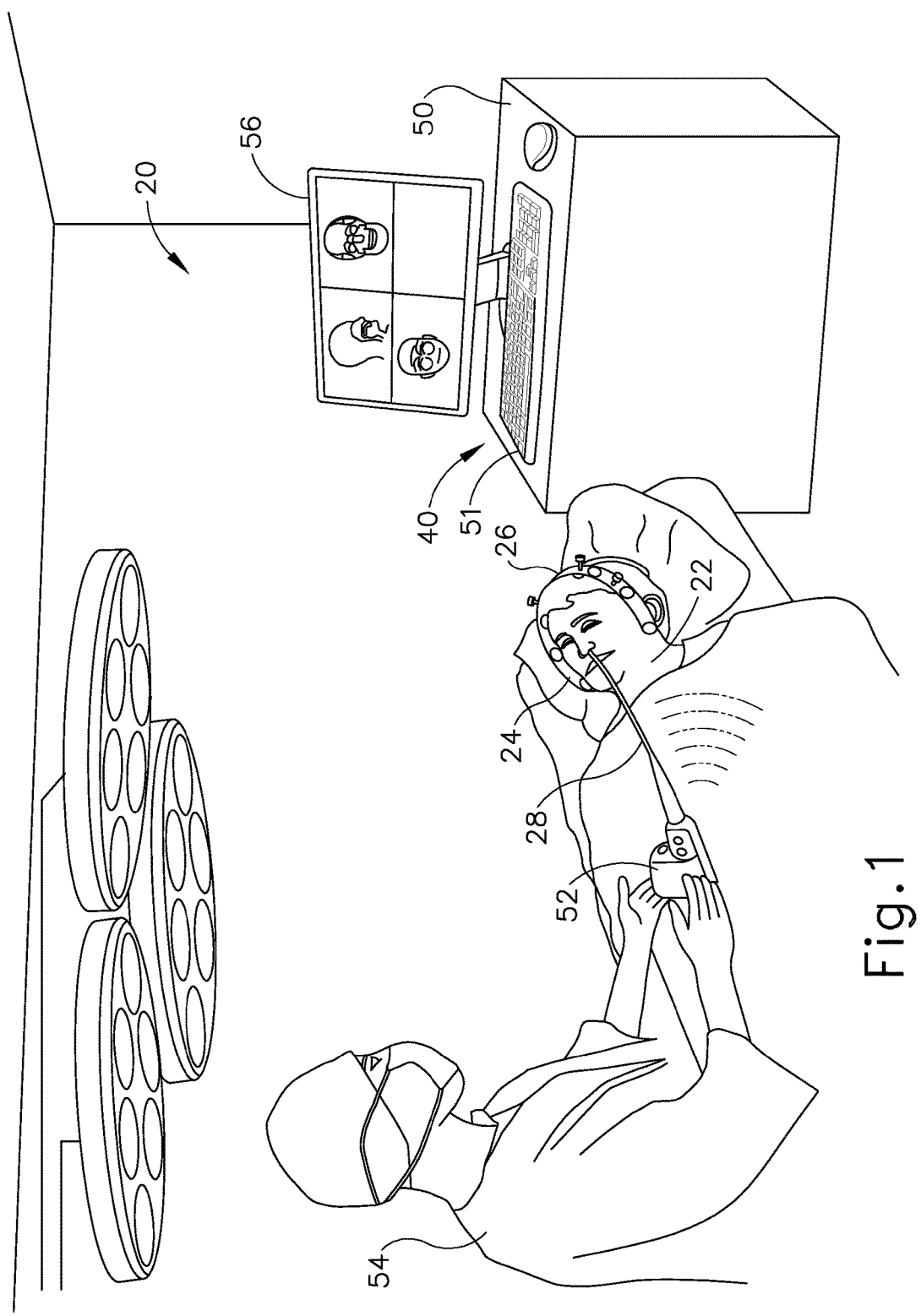
FIG. 1 depicts a schematic view of an exemplary sinus surgery system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery System

FIG. 1 shows an exemplary sinus surgery system (20) while FIG. 2 shows the head of a patient (22) undergoing surgery with system (20). In the present example, system (20) is used during a sinuplasty procedure on the patient (22), though it should be understood that system (20) may be readily used in various other kinds of procedures. In the present example, before the sinuplasty procedure begins, a set of magnetic field generators (24) are fixed to the head of the patient (22). Field generators (24) are incorporated into a frame (26), which is clamped to the head of the patient (22). As is explained below, field generators (24) enable tracking of the position of a guidewire (28) that is inserted into the nasal sinus of the patient (22). While field generators (24) are secured to the head of the patient (22) in this example, it should be understood that field generators (24) may instead be positioned at various other suitable locations and on various other suitable structures. By way of example only, field generators (24) may be mounted on an independent structure that is fixed to a table or chair on which the patient (22) is positioned, on a floor-mounted stand that has been locked in position relative to the head of the patient (22), and/or at any other suitable location(s) and/or on any other suitable structure(s).

Elements of system (20), including field generators (24), are controlled by a system processor (40) in this example. Processor (40) comprises a processing unit communicating with one or more memories. Processor (40) of the present example is mounted in a console (50), which comprises operating controls (51) that include a keypad and/or a pointing device such as a mouse or trackball. Console (50) also connects to other elements of system (20), such as a proximal end (52) of guidewire (28). A physician (54) uses the operating controls to interact with processor (40) while performing the procedure. Also during the procedure, processor (40) presents results produced by system (20) on a screen (56).

Processor (40) uses software stored in a memory of the processor to operate system (20). The software may be downloaded to processor (40) in electronic form, over a network, for example, or it may, alternatively or additionally, be provided and/or stored on non-transitory tangible media, such as magnetic, optical, or electronic memory. Processor (40) uses the software, inter alia, to operate and calibrate field generators (24). Field generators (24) are operated so as to transmit alternating magnetic fields of different frequencies into a region in proximity to frame (26). Prior to being placed on the patient (22), field generators (24) in frame (26) may be calibrated by positioning a coil (not shown) in the region in known locations and orientations relative to frame (26). Signals are induced in the calibration coil by the alternating magnetic fields, and processor (40) acquires and records the signals. Processor (40) then formulates a calibration relationship between the locations and orientations of the calibration coil, and the recorded signals for these locations and orientations.

Once the calibration relationship has been formulated, frame (26) may be placed on the head of the patient (22). Alternatively, as noted above, some versions may provide field generators (24) on structures other than frame (26). In the present example, however, after frame (26) has been placed on the head of the patient (22), frame (26) is fixed in position and registered with external features of the head of the patient (22), for example by imaging the head of the patient (22) with the attached frame (26) from a number of different angles. The frame (26) registration also registers the field generators (26) with the external features of the patient (22). Alternatively or additionally, the registration may include placing a coil in one or more known locations and orientations with respect to the external features of the patient (22) as well as with frame (26). The CARTO® 3 System by Biosense-Webster, Inc., of Diamond Bar, Calif., uses a system similar to that described herein for finding the location and orientation of a coil in a region irradiated by magnetic fields.

In addition to registering with the external features of the patient (22), the registration of the present example further includes registration with an image of the sinuses of the patient (22). In some instances, this image of the sinuses of the patient (22) has been acquired prior to a projected sinuplasty procedure. The preexisting image of the sinuses of the patient (22) may comprise a CT (computerized tomography) image, an MRI (magnetic resonance imaging) image, an ultrasound image, a combination of such images, and/or one or more images captured using any other suitable imaging modality. It should be understood that, regardless of how the image of the sinuses of the patient (22) has been acquired, frame (26) is in registration with both the sinuses of the patient (22) and the external features of the patient (22) in the present example.

FIGS. 3A-3B show guidewire (28) of the present example in greater detail. Guidewire (28) comprises an outer coil (80) having an internal lumen (82). By way of example only, coil (80) may be formed from non-ferromagnetic material, such as 316 stainless steel, titanium, cobalt-chrome, nitinol, MP35N steel alloy, and/or any other suitable materials. In some versions, the nominal external and internal diameters of coil (80) are 0.9 mm and 0.6 mm respectively. Guidewire (28) has a distal end (30) and a proximal end (32).

A tapered nitinol core-wire (84) traverses the length of lumen (82). Core-wire (84) has a distal end (86) with a smaller outer diameter than the outer diameter of the proximal end (88) of core-wire (84). The taper of core-wire (84) may be formed by centerless grinding and/or any other suitable technique(s). In some versions, a the outer diameter of proximal end (32) is in a range of 0.25 mm to 0.35 mm; while the outer diameter of distal end (86) is between 0.01 mm and 0.015 mm. Also in some versions, core-wire (84) has a length of approximately 10 cm. Core-wire (84) provides stability to the shape of guidewire (28) by being attached to outer coil (80) in at least two locations (e.g., by soldering, etc.). With core-wire (84) attached to outer coil (80), core-wire (84) provides flexural and torsional characteristics to guidewire (28) that, inter alia, prevent guidewire (28) from "winding up" when the operator rotates proximal end (52). The superelasticity of the nitinol allows guidewire (28) to undergo considerable bending while still being able to return to its unbent state.

In addition to core-wire (84), an optic fiber (90) is inserted into lumen (82) so as to traverse the length of lumen (82). A distal end (92) of optic fiber (90) is configured to be in proximity to a transparent lens (96), which is connected to, and which acts as a distal termination for, outer coil (80). A lamp (not shown) or other light source is coupled to a proximal end (98) of optic fiber (90) and is operated by processor (40) so as to illuminate lens (96) with visible light. Optic fiber (90) may comprise a single strand of fiber; or two or more strands of optical fibers. By way of example only, optic fiber (90) may be formed of plastic or glass. In some versions, optic fiber (90) comprises two plastic strands each having a diameter of 250 microns. In some other versions, optic fiber (90) comprises a single glass strand having a diameter of 150 microns or 200 microns.

Prior to insertion of optic fiber (90) into lumen (82), a magnetic field sensing coil (100) is wound around distal end (92) of optic fiber (90), so that after insertion into lumen (82), sensing coil (100) is positioned at distal end (30) of guidewire (28). Sensing coil (100) thus has an internal diameter corresponding to the external diameter of optic fiber (90). In some versions, there is a small gap (e.g., approximately 25 microns) between the internal circumference of sensing coil (100) and the external circumference of optic fiber (90). In some versions, sensing coil (100) has an external diameter of 0.45 mm, although other versions may have coil external diameters larger or smaller than 0.45 mm. In the present example, the two ends of sensing coil (100) are connected by conducting wires (104), which traverse the length of lumen (82). Conducting wires (104) are connected to circuitry in console (50), which is configured to enable processor (40) to measure and record signal levels generated by the two ends of sensing coil (100). Alternatively, the signal levels may be at least partially conveyed wirelessly to the circuitry in console (50).

Figure 4A:
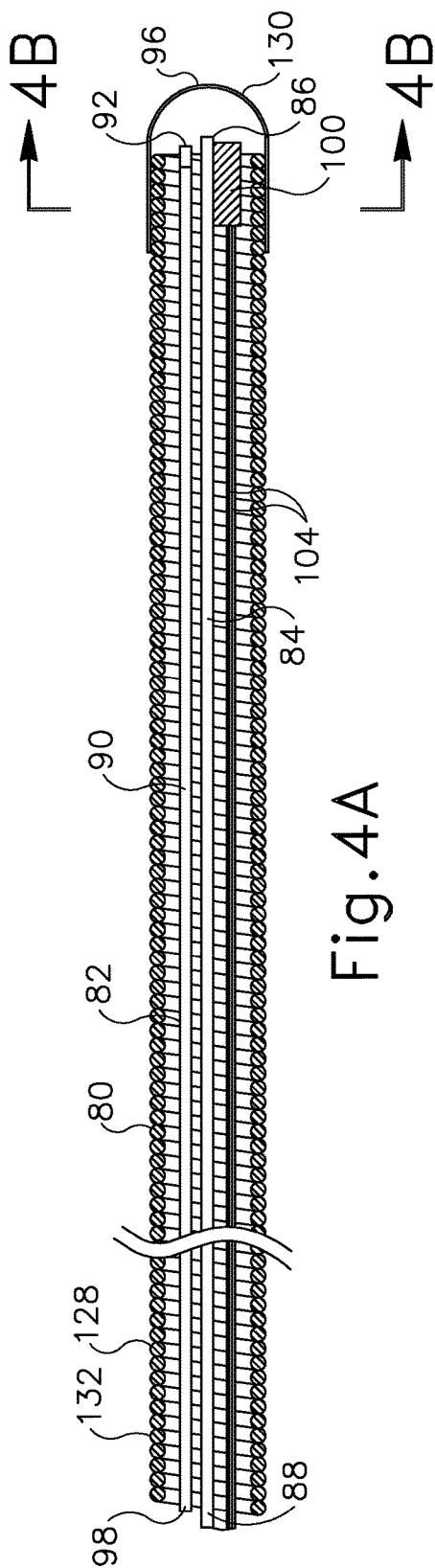
FIG. 4A depicts a cross-sectional side view of another exemplary guidewire that may be used with the sinus surgery system of FIG. 1.
Figure 4B:
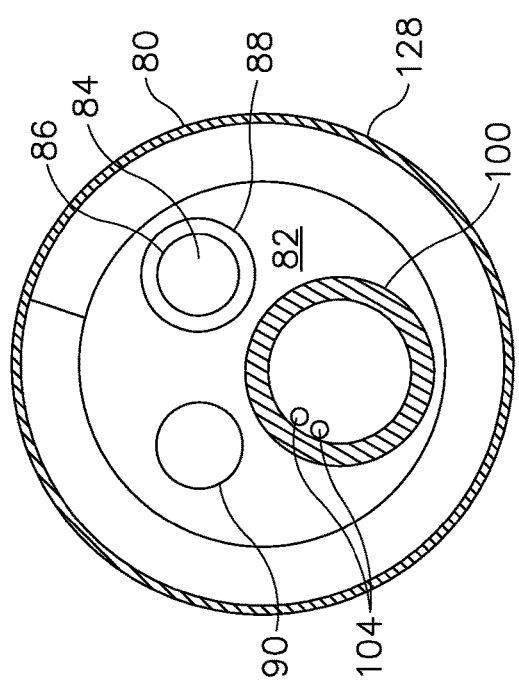
FIG. 4B depicts a cross-sectional end view of the guidewire of FIG. 4A, taken along line 4B-4B of FIG. 4A.

FIGS. 4A-4B show an exemplary alternative guidewire (128). Guidewire (128) has a distal end (130) and a proximal end (132). Apart from the differences described below, the operation of guidewire (128) is generally similar to that of guidewire (28) (FIGS. 3A-3B), and elements indicated by the same reference numerals in both guidewires (28, 128) are generally similar in construction and in operation. Thus, guidewire (128) may be used in place of guidewire (28) in system (20).

In contrast to guidewire (28), sensing coil (100) in guidewire (128) is not wound around optic fiber (90). Sensing coil (100) is still positioned within lumen (82) at distal end (130) of guidewire (128). However, sensing coil (100) is separate from both core-wire (84) and optic fiber (90) in this example. Signal levels from sensing coil (100) are transferred to circuitry, described above with reference to FIGS. 3A-3B, enabling processor (40) to measure and record the signal levels. As is also described above, the transfer may be via wires (104) or wirelessly.

Guidewire (128) also comprises tapered core-wire (84), which extends the length of lumen (82). As with guidewire (28), core-wire (84) acts to stabilize guidewire (128).

FIGS. 5A-5B show another exemplary alternative guidewire (228). Guidewire (228) has a distal end (230) and a proximal end (232). Apart from the differences described below, the operation of guidewire (228) is generally similar to that of guidewire (28) (FIGS. 3A-3B), and elements indicated by the same reference numerals in both guidewires (28, 228) are generally similar in construction and in operation. Thus, guidewire (228) may be used in place of guidewire (28) in system (20).

In guidewire (228), sensing coil (100) is configured to encircle distal end (86) of core-wire (84). An inside diameter of sensing coil (100) is larger than an external diameter of core-wire (84). Sensing coil (100) may be fixedly secured to core-wire (84) using any convenient means, such as epoxy cement, etc. Signal levels generated by sensing coil (100) are transferred to processor (40), substantially as described above for guidewires (28, 128). Some versions of guidewire (228) include an optic fiber, similar in functionality and characteristics to optic fiber (90), located in and traversing the length of lumen (82). Alternatively, as illustrated in FIGS. 5A-5B, guidewire (228) may simply lack optic fiber (90).

In an exemplary sinuplasty procedure, a guidewire such as guidewire (28, 128, 228) is inserted into a nasal sinus. The circuitry coupled to sensing coil (100) acquires signals from sensing coil (100), while field generators (24) are transmitting their magnetic fields. Processor (40) applies the calibration relationship referred to above to the signals, and together with the registration also described above finds the location and orientation of sensing coil (100). An indication of the location and orientation of sensing coil (100), i.e., of distal end (30) of guidewire (28, 128, 228), may be overlaid onto a registered, preexisting image of the sinuses of the patient (22). The composite image, of the sinuses of the patient (22) and distal end (30) of guidewire (28, 128, 228), may be displayed to physician (54) on screen (56) (FIG. 1). A more detailed description of such a use of a guidewire (28, 128, 228) in real-time surgery is provided with respect to the flowchart of FIG. 6, below.

Figure 6:
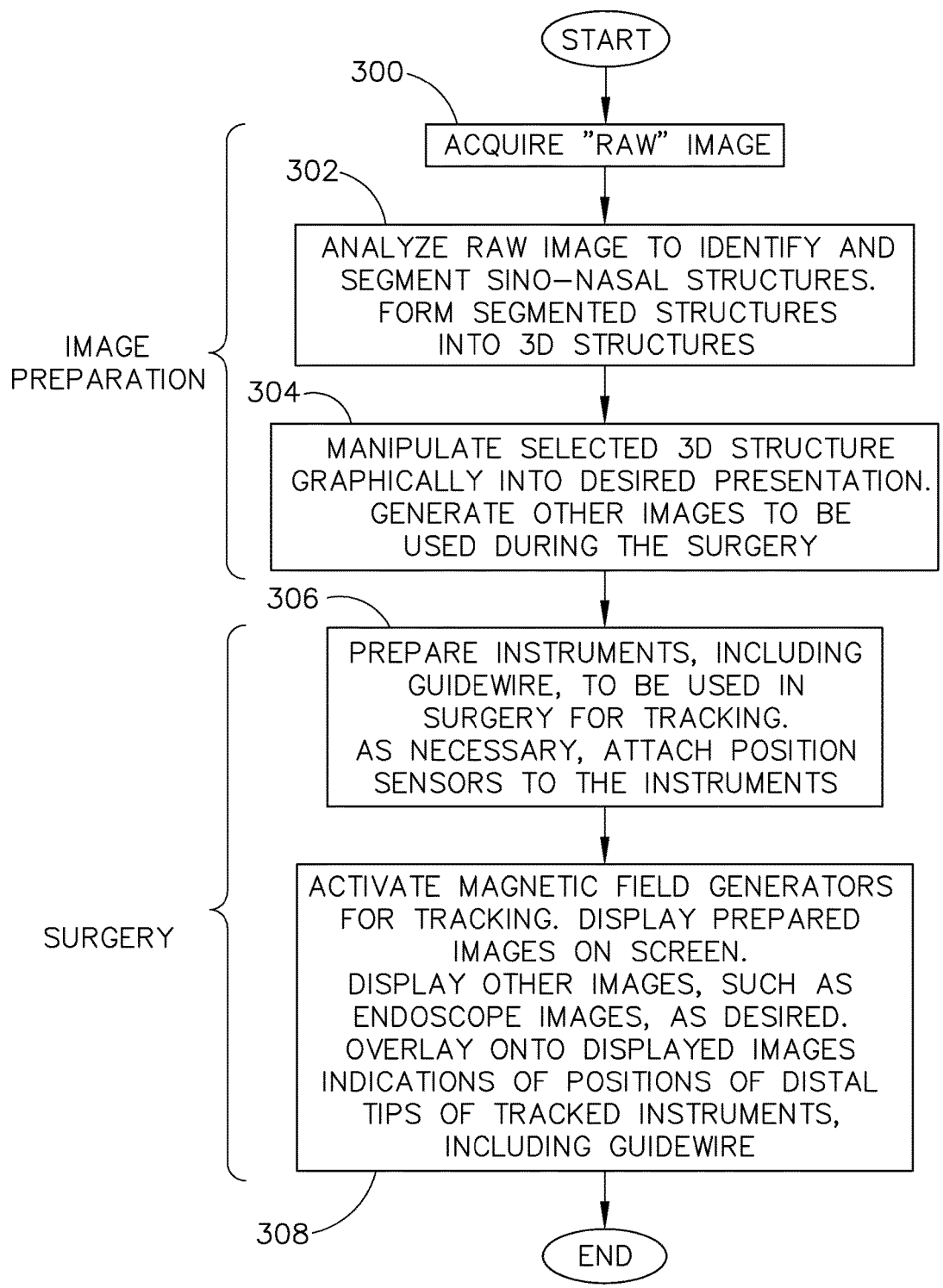
FIG. 6 depicts a flowchart showing steps of an exemplary process that may be performed using the sinus surgery system of FIG. 1.

FIG. 6 shows a flowchart of exemplary steps that may be taken using system (20) to perform image guided nasal sinus surgery. In the present example, the surgery is assumed to be performed on the ostium and outflow tract of a peripheral sinus, but those having ordinary skill in the art will be able to adapt the description, mutatis mutandis, for other various types of sinus surgery. The steps of the flowchart of FIG. 6 assume that the distal end (30) of guidewire (28, 128, 228) is tracked in real-time during the course of the surgery, by the magnetic tracking system described above. For clarity, in the flowchart description hereinbelow guidewire (28) is assumed to be used, and those having ordinary skill in the art will be able to modify the description for the use of other guidewires, such as guidewires (128, 228).

The distal tips of other instruments used during the surgery, such as the distal tip of an endoscope, the distal tip of a guide catheter, the distal tip of a dilation catheter, and/or other portions of such instruments and/or other kids of instruments, may also be tracked by the magnetic tracking system by incorporating respective coils into the instrument distal tips for flexible or rigid instruments, as is known in the art. Such instruments, which may typically be used for rhinological surgery, including Functional Endoscopic Sinus Surgery (FESS) and balloon-assisted FESS, i.e., balloon sinuplasty, are commercially available.

It should therefore be understood that guidewires (28, 128, 228) are just an illustrative example of an instrument that may incorporate a sensing coil (100). Various other kinds of instruments that are used in ENT procedures and that may readily incorporate a sensing coil (100) will be apparent to those of ordinary skill in the art in view of the teachings herein. It should also be understood that, for rigid instruments, sensing coil (100) may alternatively be positioned in a proximal portion of the instrument, provided that the magnetic tracking system has been programmed to make the spatial adjustments required to convert the signals received from sensing coil (100). Such a method for tracking is also known in the art.

In a preparatory step (300) a "raw" image of the anatomy to be operated on is acquired. The raw image may comprise a CT image, an MRI image, or a US image, of the cranium. In some instances more than one such image is combined and the composite image produced, after registration of the combined images, is used as the raw image. Images are typically in a Digital Imaging and Communications in Medicine (DICOM) format. Of course, any other suitable format may be used. Various suitable imaging modalities, imaging systems, and image formats will be apparent to those of ordinary skill in the art in view of the teachings herein.

In a first analysis step (302), the raw image is analyzed to isolate sino-nasal structures in the image. The analysis applies recognition algorithms to point clouds derived from the images so as to generate the different structures. The algorithms are used to segment the image, and to form the segmented sections into three-dimensional (3D) structures.

By way of example only, the algorithms used during the analysis step (302) may be based on "seeded region growing" algorithms such as those described in the paper "Comparison of 3D Segmentation Algorithms for Medical Imaging," by Hakan et al., published in the Twentieth IEEE International Symposium on Computer-Based Medical Systems, 2007, CBMS '07, which is incorporated herein by reference. Alternatively or additionally, the recognition referred to herein may be implemented using commercially available software, such as the OsiriX 6.5 image processing software produced by Pixmeo of Bernex, Geneva, Switzerland, or the Mimics software produced by Materialise Inc. of Leuven, Belgium. Other suitable algorithms that may be used will be apparent to those of ordinary skill in the art in view of the teachings herein.

The points within the three-dimensional structures generated in the first analysis step (302) have coordinates that enable any given structure to be transformed. For example, a given structure may be translated or rotated, or other types of transformation may be applied to the structure.

In an image manipulation step (304), the three-dimensional structures generated in step (302) are presented to the physician (54) on a screen, herein assumed by way of example to be screen (56). The physician (54) uses operating controls (51) to manipulate the image so that the region to be operated on is clearly visible. To this end the physician (54) may rotate, pan, and/or zoom the image, and/or generate one or more cross-sections of the image. In addition, the physician (54) may vary the transparency and/or color of the different structures. The manipulation may include highlighting of a region that includes the region to be operated on. For the outflow tracts considered here, such highlighting may conveniently be achieved by applying a sinus outflow tract recognition algorithm to the manipulated image. The recognition may use an algorithm similar to that referred to above in step (302), and/or may be implemented using the commercial software also referred to above.

Other images that may be generated in step (304) include displays of planned surgical steps as described below, paths to be taken by instruments as described below, and structures in proximity to the outflow tracts.

Step (304) concludes an image preparation phase that is implemented prior to performance of the nasal sinus surgery. The following steps of the flowchart describe actions that may be taken during the surgery.

In an instrument preparation step (306), instruments to be used in the surgery are prepared so that they can be tracked during the surgery. The instruments include guidewire (28), as described hereinabove, which can be tracked by system (20) using sensing coil (100). The instruments may also include an endoscope, one or more flexible instruments, one or more catheters, and/or any one or more of the following: grasping forceps, cutting forceps, including Blakesly forceps and Blakesly throughcutting forceps, irrigation cannulae, suction cannulae, including Frazier and Yankauer suction cannulae, balltipped probe, sinus seeker, Freer elevator, Coddle elevator, other elevators, J-curettes or other curettes, punches, including mushroom punches, injection needles, needle drivers, monopolar or bipolar electrocautery probes, RF ablation probes, laser-energy transmitting probes, powered or manual microdebriders, shavers, drills, or burrs. Other suitable instruments will be apparent to those of ordinary skill in the art in view of the teachings herein.

As noted above, any such instruments may incorporate a sensing coil (100) to enable tracking of the positioning of the instrument. Such sensing coils (100) may be configured to be tracked by system (20), using magnetic fields from field generators (24) to induce tracking signals in sensing coils (100). Alternatively, the instruments may include sensors that are configured to use the Hall effect to generate the tracking signals. In the case of rigid instruments, the sensors may be mounted on a proximal portion of the instrument in a known fixed spatial relation with the instrument distal portion. By way of example only, a sensing coil (100) or other sensor may be mounted on or in the distal portion of the instrument (e.g., particularly if the instrument is flexible). In addition or in the alternative, a sensing coil (100) or other sensor may be mounted on or in the proximal portion of the instrument (e.g., particularly if the instrument is rigid).

Regardless of where sensing coil (100) or other sensor is positioned, sensing coil (100) or other sensor may be built into an instrument at the time of manufacture. In other instances, it may be desirable to attach one or more sensing coils (100) or other sensors to an instrument prior to use of that instrument in surgery. A method for performing such attachment is described in U.S. Pat. No. 8,190,389, entitled "Adapter for Attaching Electromagnetic Image Guidance Components to a Medical Device," issued May 29, 2012, the disclosure of which is incorporated by reference herein; and U.S. Pub. No. 2012/0245456, entitled "Adapter for Attaching Electromagnetic Image Guidance Components to a Medical Device," published Sep. 27, 2012, issued as U.S. Pat. No. 9,198,736 on Dec. 1, 2015, the disclosure of which is incorporated by reference herein.

In a final real-time procedure step (308), the physician (54) activates field generators (24) to begin the instrument tracking process. The physician (54) also displays one or more images, in some instances multiple image panels, on screen (56). The images displayed may include the real-time image formed by an endoscope used in the procedure, as well as the images prepared and generated in step (304). It should therefore be understood that the presentation of multiple image panels on screen (56) may enable the physician (54) to view several images from different sources simultaneously.

An indication of the location and orientation of the endoscope distal end may be overlaid, in registration, on the outflow tracts image generated in step (304). Similarly, an indication of the location and orientation of the distal end (30) of guidewire (28) may also be overlaid, in registration, with the outflow tracts image. As other instruments are introduced into the patient, their location and orientation may also be overlaid on the outflow tracts image.

The endoscope image referred to above may have superimposed upon it the image of the outflow tracts generated in image manipulation step (304), as well as one or more images of other structures that may have been generated in the image manipulation step (304).

In some versions, the images displayed on screen (56) may be manipulated by the physician (54) so as to improve the visibility of desired portions of the image, and so as to reduce "noise" in the presented image. Such manipulation may include the physician being able to render sections of the image (e.g., outer sections) to be at least partially transparent, so that inner sections of the image, including the indications of the distal tips of instruments used, including guidewire (28), are more visible. Alternatively or additionally, the manipulation may include the physician applying "false" color to sections of the image representing specific anatomical structures that have been segmented in step (302). In some versions, the physician (54) uses controls (51) to manipulate or adjust the images on screen (56). In addition or in the alternative, system (20) may be configured to enable the physician (54) to manipulate or adjust the images on screen (56) using voice activation and/or other non-tactile methods of activation.

Because the location and orientation of distal end (30) of guidewire (28) are known in real-time, cross-sections or slices of the anatomy in proximity to distal end (30) of guidewire (28) may be generated and displayed on screen (56) by system (20). For example, a cross-section of the anatomy ahead of distal end (30) of guidewire (28) may be displayed. Other images that may be presented on screen (56) include displays of planned surgical steps, paths to be taken by instruments, and structures in proximity to the structure being operated on. As stated above, such images are typically generated in image manipulation step (304). Further examples of how such images may be generated and presented will be described in greater detail below.

II. Exemplary Image Guided Surgical Tutorial

In some instances, it may be desirable to provide a physician (54) with a surgical plan or instructions on how to perform an ENT procedure (e.g., sinuplasty, etc.) on a patient (22), with such instructions being customized based on the unique anatomy of that particular patient (22). As noted above with respect to manipulation step (304) shown in FIG. 6, processor (40) may be capable of manipulating image data associated with the patient (22) to provide such instructions on images that depict the unique anatomy of the patient (22). Moreover, processor (40) may be able to determine how best to perform the selected procedure on the patient (22) based on the unique anatomy of the patient, and may provide such customized instructions via images generated during manipulation step (304). In addition or in the alternative, a physician (54) may provide further input that is used to generate customized instructions via images generated during manipulation step (304).

Regardless of whether the instructional images are generated automatically and/or based on input from the physician (54), such instructional images may be provided in the form of a series of still images, a video "fly through," and/or any other suitable form. For shorthand purposes, the output will be referred to herein as "instructional images," with it being understood that such images may include still images, moving images (e.g., video, animations, etc.), combinations thereof, and/or any other suitable kinds of images. It should also be understood that instructional images may be two-dimensional, three-dimensional, and/or combinations thereof.

Such instructional images may be rendered through one or more image panels on screen (56). Moreover, such instructional images may be automatically updated as the physician (54) performs the procedure. For instance, system (20) may continuously track movement of instruments used by the physician (54), determine the stage of the procedure based on such tracked movements, and update the instructional images based on the current stage of the procedure. In addition or in the alternative, the physician (54) may provide input via controls (51), voice activation, and/or some other means to inform system (20) of the current stage of the ENT procedure. Specific examples of how instructional images may be provided will be described in greater detail below. It should be understood that the following examples are merely illustrative. Further examples and variations will be apparent to those of ordinary skill in the art in view of the teachings herein.

A. Exemplary Process to Automatically Generate Customized Operation Plan

Figure 7:
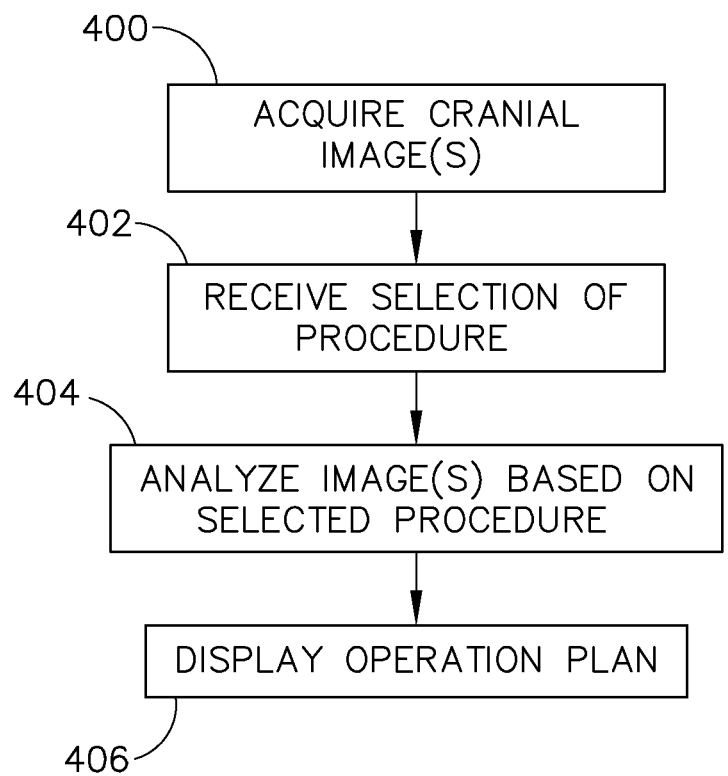
FIG. 7 depicts a flowchart showing steps of an exemplary process that may be used to generate an operation plan for a surgical procedure.

FIG. 7 shows an exemplary process that may be used to provide a surgical plan for a physician (54), using data from system (20) and/or from other sources. It should be understood that the process of FIG. 7 may be incorporated into the process of FIG. 6. For instance, the process of FIG. 7 may be performed as a subroutine within manipulation step (304) shown in FIG. 6. Alternatively, the process of FIG. 7 may be integrated into some other larger process or may be performed as a stand-alone process. The process of FIG. 7 will be discussed below as being performed by system (20), though it should be understood that the process of FIG. 7 may be performed by any other suitable system having any other suitable components in any other suitable configuration. By way of further example only, at least part of the process of FIG. 7 may be performed through the system (1000) of FIG. 14 as described below. It should also be understood that part of the process of FIG. 7 may be performed on one system, while another part of the process of FIG. 7 is performed on another system.

At an initial step (400), a cranial image (or images) of the patient (22) is obtained. It should be understood that this is a cranial image of the same patient (22) on whom the ENT surgical procedure will be performed. This cranial image (or images) may be obtained using MRI, CT, and/or any other suitable imaging modality or modalities. At least some image data may be created or supplemented by data provided through a mapping process performed using system (20), where a probe having a sensing coil (100) is maneuvered through the nasal cavity of the patient (22) to establish geometry of anatomical structures within the nasal cavity of the patient (22). In addition or in the alternative, the image data may be provided from another source (e.g., from scanning performed at some other time in the past and/or at some other facility, etc.).

In some instances, two or more images are provided in step (400). By way of example only, the images may be provided as DICOM (Digital Imaging and Communications in Medicine) files and imported into processor (40). Processor (40) may include software that is specialized to evaluate the layout of the anatomy of the nasal passages and paranasal sinuses based on the images. In some examples, the images may comprise a three-dimensional image that is manipulable using a graphical user interface. The three-dimensional image may be obtained by preparing a segmented three-dimensional model. In versions that employ use of a three-dimensional model, the three-dimensional model may be preexisting and thus imported into processor (40) as a three-dimensional model. Alternatively, processor (40) may generate the three-dimensional model based on two-dimensional image data that is imported into processor (40). Of course, any other suitable technique may be used to generate the three-dimensional model. It should also be understood that some versions may not necessarily require the generation of a full three-dimensional model.

In the next step (402) of the process shown in FIG. 7, processor (40) receives an input from the physician (54) indicating the particular type of procedure that the physician (54) wishes to perform on the patient (22). For instance, the physician (54) may provide this input using operating controls (51), using voice commands, and/or using any other suitable form of input. System (20) may enable the physician (54) to select from an extensive list of various ENT procedures, including but not limited to dilation of the frontal recess, dilation of a maxillary sinus ostium, dilation of a sphenoid sinus ostium, dilation of a Eustachian tube, formation of an opening in an ethmoid bulla, and/or various other ENT procedures. In some variations, processor (40) is only configured to provide a surgical plan for sinuplasty procedures, such that the physician (54) simply selects which passageway (e.g., the frontal recess, the maxillary sinus ostium, the sphenoid sinus ostium, etc.) the sinuplasty procedure will be performed in.

Once system (20) has received the necessary image(s) (step (400)) that are unique to the patient (22) at hand, as well as the input from the physician (54) (step (402)) indicating the particular type of procedure that the physician (54) wishes to perform on the patient (22), the system (20) may then perform an analysis step (404). During this analysis step (404), the software (e.g., as executed through processor (40)) evaluates the layout of the anatomy of the nasal passages and paranasal sinuses of the patient (22) based on the cranial image(s) that was/were imported as part of step (400) in relation to data associated with the medical procedure selected in step (402). It should be understood that the data associated with the various medical procedures available for selection during step (402) may be stored locally in system (20) and/or may be stored remotely on one or more remote servers, etc. Regardless of where such data is stored, processor (40) may access and process the data associated with the medical procedure selected in step (402) and determine how to best implement that procedure on the unique anatomy of the patient (22) as represented by the cranial image(s) that was/were imported as part of step (400). This processing may include establishing a succession of translational and rotational coordinates with reference to the image(s) that was/were imported as part of step (400).

Once processor (40) has completed the analysis step (404), processor (40) may generate an output to the physician (54) to thereby display an operation plan (step (406)) that is tailored to the particular patient (22). The operation plan that is output at step (406) may provide a "roadmap" or step-by-step instructions to the physician (54) on how to perform the selected ENT procedure. By way of example only, when the selected ENT procedure comprises a sinus drainage passageway dilation procedure, the operation plan that is output at step (406) may include a roadmap for performing at least some (if not all) of the following acts on the patient (22): (i) positioning a guide member (e.g., guide catheter, guide rail, guide probe, etc.) within the nasal cavity of the patient, (ii) advancing a guidewire relative to the guide member to insert the guidewire through a paranasal sinus drainage passageway (e.g., a paranasal sinus ostium, the frontal recess, etc.), (iii) advancing a dilator along the guidewire to position the dilator in the paranasal sinus drainage passageway, and (iv) expanding the dilator to dilate the drainage passageway, to thereby enable ventilation and drainage and restore normal outflow of mucus based on the natural directions of mucociliary transport. Of course, this is just one merely illustrative example of an ENT procedure that may be the subject of an operation plan that is output at step (406). Various other kinds of ENT procedures that may be the subject of an operation plan that is output at step (406) will be apparent to those of ordinary skill in the art in view of the teachings herein.

Various examples of how an operation plan may be visually displayed (step (406)) will be described in greater detail below with reference to FIGS. 9-13C. Other examples will be apparent to those of ordinary skill in the art in view of the teachings herein.

B. Exemplary Process to Manually Generate Customized Operation Plan

Figure 8:
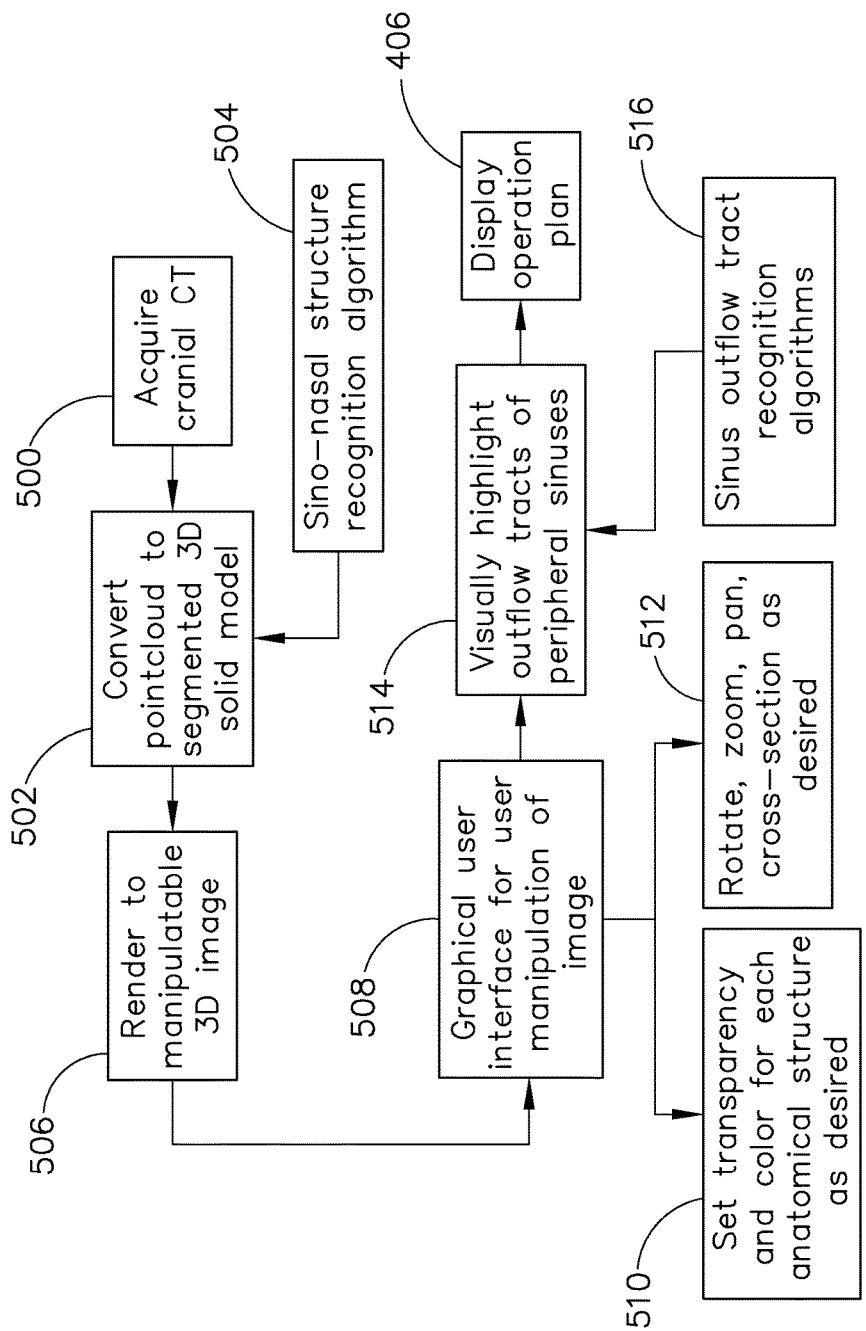
FIG. 8 depicts a flowchart showing steps of another exemplary process that may be used to generate an operation plan for a surgical procedure.

FIG. 8 shows another exemplary process that may be used to provide a surgical plan for a physician (54), using data from system (20) and/or from other sources. It should be understood that the process of FIG. 8 may be incorporated into the process of FIG. 6. For instance, the process of FIG. 8 may be performed as a subroutine within manipulation step (304) shown in FIG. 6. Alternatively, the process of FIG. 8 may be integrated into some other larger process or may be performed as a stand-alone process. The process of FIG. 8 will be discussed below as being performed by system (20), though it should be understood that the process of FIG. 8 may be performed by any other suitable system having any other suitable components in any other suitable configuration. By way of further example only, at least part of the process of FIG. 8 may be performed through the system (1000) of FIG. 14 as described below. It should also be understood that part of the process of FIG. 8 may be performed on one system, while another part of the process of FIG. 8 is performed on another system.

As noted above with reference to the analysis step (404) of FIG. 7, system (20, 510) may include a database of stored ENT medical procedures that may be referenced in combination with the image(s) that was/were imported as part of step (400). In the process of FIG. 8, such stored ENT medical procedures may be initially created. In other words, the process shown in FIG. 8 may be performed without necessarily a pre-existing database of stored ENT medical procedures. The process of FIG. 8 may be performed by the physician (54) before the same physician (54) performs the ENT medical procedure on the patient (22). As another merely illustrative example, the process of FIG. 8 may be performed as part of physician training, with a training physician (54) performing the process of FIG. 8 while a trainee physician (54) carries out the operation plan or instructions that are generated (step (406)) based on the input that was provided by the training physician (54) during the process of FIG. 8.

At an initial step (500), a cranial image (or images) of the patient (22) is obtained. It should be understood that this is a cranial image of the same patient (22) on whom the ENT surgical procedure will be performed. This cranial image (or images) may be obtained using MRI, CT, and/or any other suitable imaging modality or modalities. At least some image data may be created or supplemented by data provided through a mapping process performed using system (20), where a probe having a sensing coil (100) is maneuvered through the nasal cavity of the patient (22) to establish geometry of anatomical structures within the nasal cavity of the patient (22). In addition or in the alternative, the image data may be provided from another source (e.g., from scanning performed at some other time in the past and/or at some other facility, etc.).

In some instances, two or more images are provided in step (500). By way of example only, the images may be provided as DICOM (Digital Imaging and Communications in Medicine) files and imported into processor (40). Processor (40) may include software that is specialized to evaluate the layout of the anatomy of the nasal passages and paranasal sinuses based on the images. In the present example, the software converts a pointcloud into a segmented three-dimensional model (step (502)). As part of this process, the software applies sino-nasal structure recognition algorithms through processor (40) (step (504)). The software ultimately generates output in the form of a manipulatable three-dimensional image (step (506)). Various suitable ways in which software may be configured to perform the above described steps (502, 504, 506) will be apparent to those of ordinary skill in the art in view of the teachings herein.

The physician (54) is then presented with a graphical user interface (GUI) to manipulate the three-dimensional image (step (508)). By way of example only, this GUI may enable the physician (54) to define a transparency and/or color for each anatomical structure as desired (step (510)). As one merely illustrative example, where the three-dimensional image is being prepared to provide an operation plan to dilate a maxillary sinus ostium, the physician may set a graphical representation of the uncinate process as being approximately 50% transparent; and color the maxillary sinus ostium red. The GUI may also enable the physician (54) to provide various kinds of markings and/or annotations within the three-dimensional image. To facilitate exploration and marking of the three-dimensional image, the GUI may further enable the physician (54) to rotate, zoom, pan, tilt, take cross-sections, or otherwise alter two-dimensional views of the three-dimensional image (step (512)).

The software of the present example also provides visual highlighting of outflow tracts of the paranasal sinuses (step (514)). In the present example, this process is automated through the application of sinus outflow tract recognition algorithms (step (516)). Various suitable ways in which software may be configured to perform the above described steps (508, 510, 512, 514, 516) will be apparent to those of ordinary skill in the art in view of the teachings herein.

Once step (514) has been completed, processor (40) may generate an output to the physician (54) to thereby display an operation plan (step (406)). As noted above, the operation plan that is output at step (406) may provide a "roadmap" or step-by-step instructions to the physician (54) on how to perform the selected ENT procedure. By way of example only, when the selected ENT procedure comprises a sinus drainage passageway dilation procedure, the operation plan that is output at step (406) may include a roadmap for performing at least some (if not all) of the following acts on the patient (22): (i) positioning a guide member (e.g., guide catheter, guide rail, guide probe, etc.) within the nasal cavity of the patient, (ii) advancing a guidewire relative to the guide member to insert the guidewire through a paranasal sinus drainage passageway (e.g., a paranasal sinus ostium, the frontal recess, etc.), (iii) advancing a dilator along the guidewire to position the dilator in the paranasal sinus drainage passageway, and (iv) expanding the dilator to dilate the drainage passageway, to thereby enable ventilation and drainage and restore normal outflow of mucus based on the natural directions of mucociliary transport. Of course, this is just one merely illustrative example of an ENT procedure that may be the subject of an operation plan that is output at step (406). Various other kinds of ENT procedures that may be the subject of an operation plan that is output at step (406) will be apparent to those of ordinary skill in the art in view of the teachings herein.

While not shown in FIG. 8, it should be understood that the software may further enable the physician (54) to perform the ENT procedure virtually using the three-dimensional image that was generated in step (506). For instance, the software may present the physician (54) with graphical representations of instruments that may be used in the ENT procedure, with such graphical representations of instruments being overlaid or otherwise integrated with the three-dimensional image. The physician (54) may manipulate the graphical representations of the instruments using any suitable input or combinations of inputs (e.g., mouse, trackpad, keyboard, joystick, touchscreen, etc.). By allowing the physician (54) to perform the ENT procedure virtually, the software enables the physician (54) to perform as many practice runs as desired in order to assist the physician (54) in finding a most appropriate technique.

Moreover, data that is captured during the virtual ENT procedure may be used to develop the operation plan that is output at step (406). In particular, when the physician (54) has successfully completed one or more steps of the virtual ENT procedure, the system may store the movements and orientations of the virtual instruments as manipulated by the physician (54) during the virtual ENT procedure, and incorporate the stored successful movements and orientations of the virtual instruments in the operation plan that is output at step (406). In other words, the physician (54) may first perfect the ENT procedure virtually on the three-dimensional model of the patient's anatomy, then rely on the operation plan that is output at step (406) in order to reenact the movements and orientations of the virtual instruments that were successful in the virtual ENT procedure when the physician (54) uses real instruments to perform the real ENT procedure on the patient (22). Various suitable ways in which the software may permit, capture, and use the results of virtual ENT procedures will be apparent to those of ordinary skill in the art in view of the teachings herein.

C. Exemplary Process to Render a Customized Operation Plan

Figure 9:
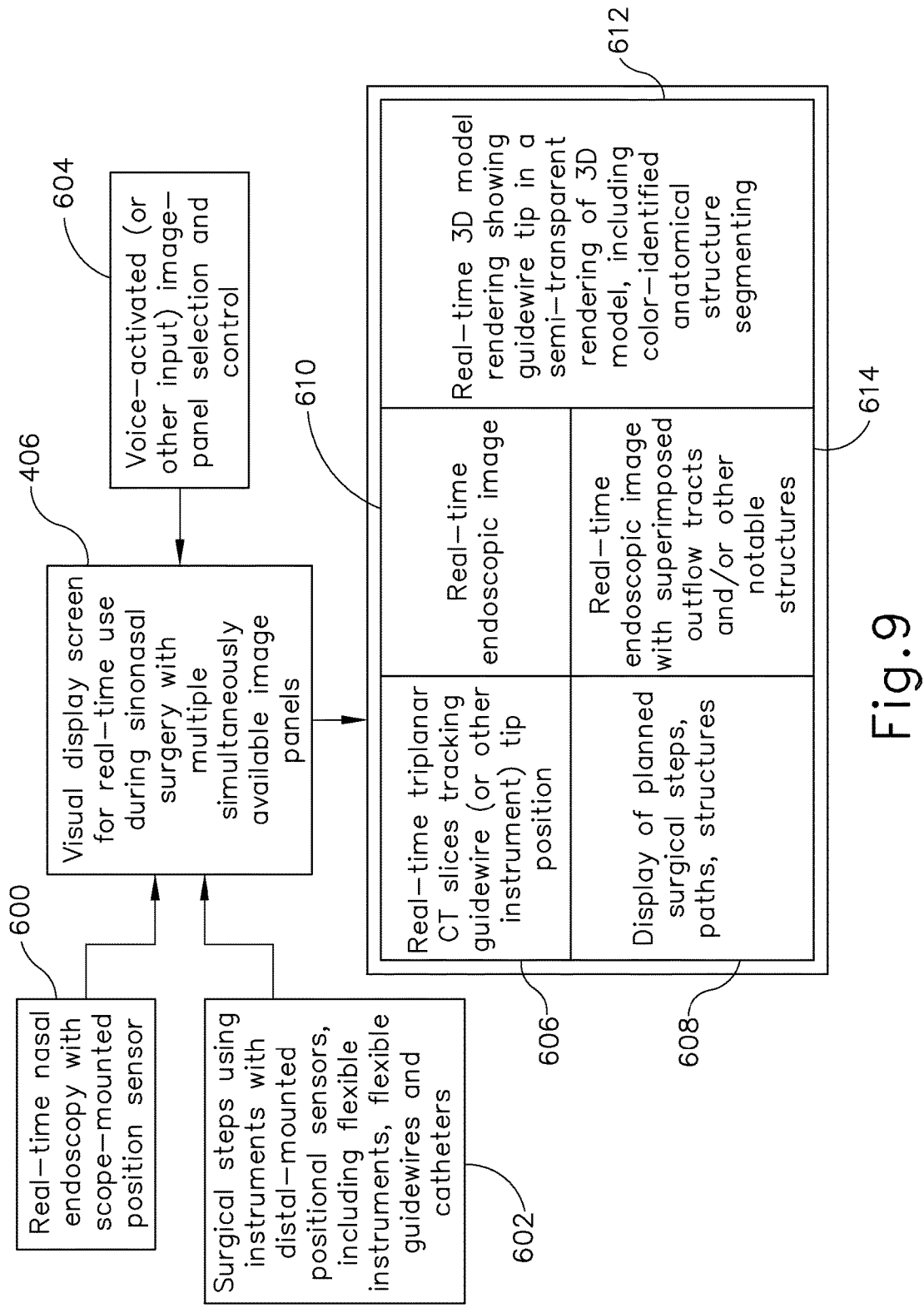
FIG. 9 depicts a flowchart showing steps of an exemplary process that may be used to render an operation plan for a surgical procedure to a physician.

As noted above, the process shown in FIG. 7 and the process shown in FIG. 8 may each generate an output to the physician (54) to thereby display an operation plan (step (406)) that is tailored to the particular patient (22). In the present example, the operation plan is provided in the form of one or more instructional images. The instructional images that are displayed in step (406) may be rendered through one or more image panels on screen (56). FIG. 9 shows exemplary steps that may be provided in conjunction with the operation plan that is presented (step (406)) to the physician (54). Examples of the kinds of instructional images that may be displayed are described in greater detail below with reference to blocks (606, 608, 610, 612, 614) of FIG. 9 and also with reference to FIGS. 10-13C.

In some instances, the ENT procedure may be performed with real visual guidance provided from an endoscope as shown in step (600). The video view from the endoscope may be combined with one or more of the instructional images that are displayed in step (406), such that the endoscopic view may be rendered through one or more image panels on screen (56). The endoscope may further include a sensing coil (100) or other sensor, such that the position of the endoscope may be tracked by system (20). The positioning data from the sensing coil (100) or other sensor may be further incorporated into the one or more of the instructional images that are displayed in step (406). For instance, a graphical representation of the endoscope may be superimposed or otherwise integrated into one or more virtual views of the sino-nasal anatomy of the patient as rendered through one or more image panels on screen (56). This may provide the physician (54) with a better sense of where the real-time position of the endoscope is within the nasal cavity, thereby providing a better context for the endoscopic view that is being provided by the endoscope itself. In some other versions, the endoscope lacks a sensing coil (100) or other sensor, such that the software presenting the instructional images does not depict or otherwise account for real-time positioning of the endoscope.

Similarly, the ENT procedure may be performed using one or more instruments that incorporate a sensing coil (100) or other sensor as described above. In such instances, positioning data from the sensing coil (100) or other sensor may be processed in conjunction with the operation plan as shown in step (602). The positioning data from the sensing coil (100) or other sensor may be further incorporated into the one or more of the instructional images that are displayed in step (406). For instance, a graphical representation of the ENT instrument may be superimposed or otherwise integrated into one or more virtual views of the sino-nasal anatomy of the patient as rendered through one or more image panels on screen (56). This may provide the physician (54) with a better sense of where the real-time position of the ENT instrument is within the nasal cavity, thereby supplementing the real endoscopic view of the ENT instrument. In some other versions, the ENT procedure is performed without any of the ENT instruments having a sensing coil (100) or other sensor, such that the software presenting the instructional images does not depict or otherwise account for real-time positioning of the ENT instruments.

Some versions may enable the physician (54) to manipulate the instructional images before and/or during a surgical procedure. For instance, the software may enable the physician (54) to rotate, pan, tilt, zoom, explode, take cross-sections, and/or perform other manipulations of the instructional images. This may enable the physician (54) to get a better sense of the precise positioning, orientation, and direction of movement for the instrument at a given stage of a medical procedure. By way of example only, the physician (54) may manipulate the instructional image using various kinds of inputs such as a mouse, trackpad, keyboard, joystick, touchscreen, etc. In addition or in the alternative, some versions may enable the physician (54) to manipulate the instructional images using voice input (step (604)). This may keep both of the physician's hands free to grasp and manipulate the endoscope and other ENT instruments during the entire ENT procedure. Various suitable ways in which voice command capabilities may be incorporated will be apparent to those of ordinary skill in the art in view of the teachings herein.

Regardless of whether and how data/commands from steps (600, 602, 604) are used to influence the instructional images, it should be understood that the instructional images may take numerous different forms. As noted above, the instructional images that are displayed in step (406) may be rendered through one or more image panels on screen (56). In other words, several instructional images may be presented to the physician (54) simultaneously. When several instructional images are presented to the physician (54) simultaneously, those several instructional images may provide views that are different from each other. Various examples of forms that the instructional images may take ware described in greater detail below with reference to blocks (606, 608, 610, 612, 614) of FIG. 9 and also with reference to FIGS. 10-13C. Any or all of the views described below with reference to blocks (606, 608, 610, 612, 614) of FIG. 9 and also with reference to FIGS. 10-13C may be presented to the physician (54) simultaneously. It should be understood that the following examples are merely illustrative. Further examples and variations will be apparent to those of ordinary skill in the art in view of the teachings herein.

By way of example only, in versions where one of the ENT instruments includes a sensing coil (100) or other sensor, one or more of the instructional images may provide views of real-time triplanar CT slices of the position of the tip of the ENT instrument, as shown in block (606). Various suitable ways in which an instructional image may depict the real-time positioning of an instrument that has a sensing coil (100) or other sensor will be apparent to those of ordinary skill in the art in view of the teachings herein.

As also shown in FIG. 9, one of the instructional images may include a display of planned ENT procedure steps, instrument paths and orientations, and anatomical structures (block (608)). Further examples of such a view will be described in greater detail below with reference to FIGS. 10-13C.

In addition, as noted above, one of the image panels on screen (56) may provide a real endoscopic view of the nasal cavity from a real endoscope (block (610)), with the endoscopic view being provided adjacent to one or more instructional images.

As another merely illustrative example, in versions where one of the ENT instruments includes a sensing coil (100) or other sensor, one or more of the instructional images may provide a real-time three-dimensional model rendering showing the position of the tip of the ENT instrument, as shown in block (612). In some such versions, the visual representations of the anatomical structures are shown semitransparently in order to prevent the visual representations of the anatomical structures from obscuring the view of the visual representation of the ENT instrument. This view may further include color-identified anatomical structure segmenting and/or other visual features that facilitate differentiation between different anatomical structures.

In versions that provide a real endoscopic view of the nasal cavity from a real endoscope, such a real endoscopic view may further include software generated visual features that are superimposed or otherwise integrated into the real endoscopic view. For instance, the software may superimpose highlighting of the sinus outflow tracts (and/or other notable anatomical structures) that are within the endoscopic field of view (block (614)). Such an enhanced endoscopic view (block (614)) may be provided in combination with or in lieu of a non-enhanced endoscopic view (block (610)).

Figure 10:
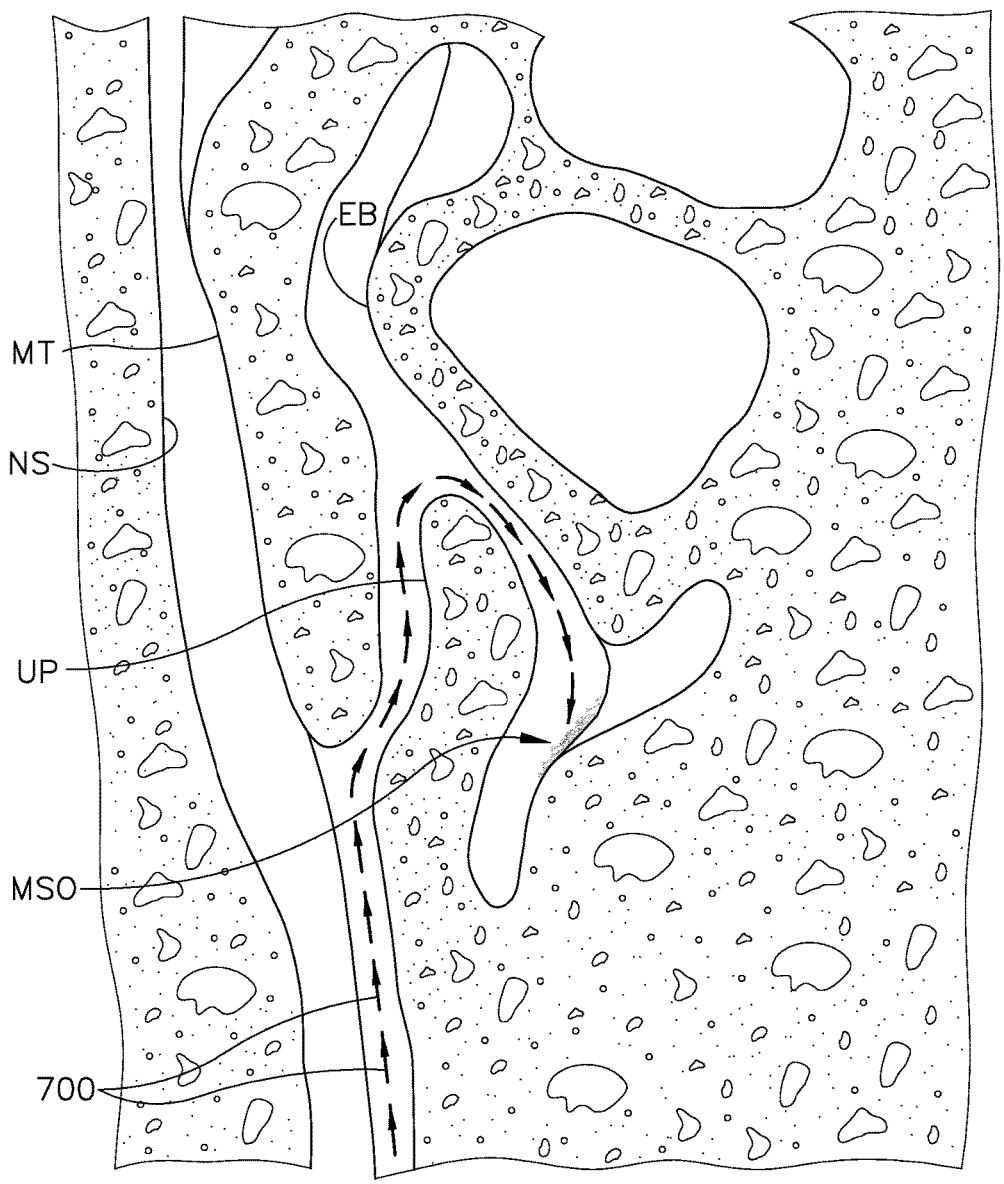
FIG. 10 depicts a superior axial cross-sectional view of a portion of a human head, showing paranasal sinus structures, that may be rendered as an instructional image in an operation plan for a surgical procedure.

FIG. 10 shows an example of one of the instructional images that may be displayed in step (406). In particular, FIG. 10 shows a superior axial cross-sectional view of anatomical structures in the nasal cavity of the patient (22). In particular, FIG. 10 depicts the nasal septum (NS), the middle turbinate (MT), the uncinate process (UP), and the ethmoid bulla (EB). It should be understood that this view would have been generated from the cranial image(s) that were acquired in step (400) of the process shown in FIG. 7 or step (500) of the process shown in FIG. 8. The view of FIG. 10 also includes a set of arrows (700) that indicate a pathway for insertion of an instrument into the maxillary sinus ostium (MSO). In some versions, the arrows (700) are all presented simultaneously and statically. In some other versions, the arrows (700) are animated to emphasize the directions of the pathway to the maxillary sinus ostium (MSO). In still other versions, a single arrow (700) is used, with the stem of single arrow bending along the tortuous path to the maxillary sinus ostium (MSO). Other suitable ways in which a cross-sectional view may depict a path toward a maxillary sinus ostium (MSO) or other anatomical structure associated with the nasal cavity will be apparent to those of ordinary skill in the art in view of the teachings herein. It should also be understood that several different cross-sectional views (e.g., along different planes) may be presented simultaneously in order to provide the physician (54) with a better sense of how the instrument path traverses three dimensions.

Figure 11:
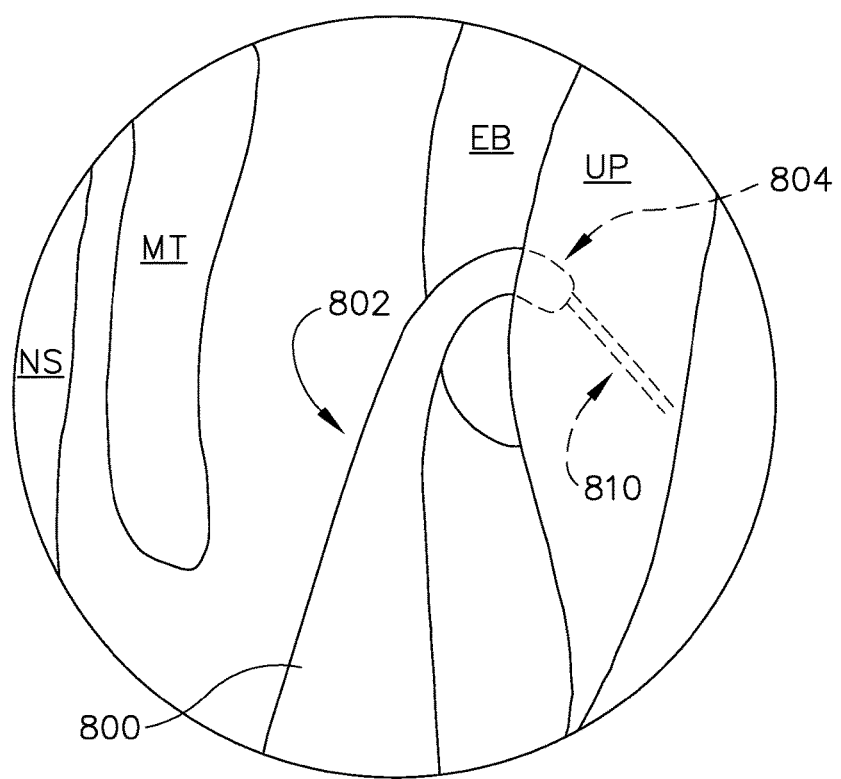
FIG. 11 depicts a virtual endoscopic view of a middle meatus of a human head, with a representation of a guide catheter and guidewire, that may be that may be rendered as an instructional image in an operation plan for a surgical procedure.

FIG. 11 shows an example of another one of the instructional images that may be displayed in step (406). In particular, FIG. 11 presents a virtual endoscopic view showing a graphical representation (800) of a guide catheter and a graphical representation (810) of a guidewire from the viewpoint of an endoscope whose line of sight is oriented toward the middle meatus of the patient (22). The view thus shows the position and orientation of graphical representation (800) in relation to graphical representations of the nasal septum (NS), the middle turbinate (MT), the ethmoid bulla (EB), and the uncinate process (UP). The view is provided with a three-dimensional perspective in order to provide the physician with a better sense of how the guide catheter that is represented by graphical representation (800) should be positioned relative to the anatomical structures.

In the example shown in FIG. 11, the instructional image is showing how to insert the guidewire into the maxillary sinus ostium. In a real endoscopic view of the same instruments and anatomy, the distal end of the guide catheter and the guidewire would be visually obscured by the uncinate process (UP). Thus, the instructional image depicts the distal end (804) of graphical representation (800) and graphical representation (810) in semi-transparent form; while depicting the proximal end (902) of graphical representation (800) in opaque form. The uncinate process (UP) is depicted in opaque form in this example. In another exemplary variation, the uncinate process (UP) is depicted in semi-transparent form. In such versions, the distal end (804) of graphical representation (800) and graphical representation (810) may be depicted in opaque form. Other suitable ways in which the instructional image may handle the obscuring of instruments by anatomical structures will be apparent to those of ordinary skill in the art in view of the teachings herein.

In some versions, the instructional image of FIG. 11 is presented simply as a still image. In some other versions, the instructional image of FIG. 11 is provided as an animation. For instance, the instructional image may start by simply showing the anatomical structures. The instructional image may then show an animation of graphical representation (800) being moved into the position shown in FIG. 11. The instructional image may then show an animation of graphical representation (810) being moved into the position shown in FIG. 11. Other suitable ways in which the instructional image of FIG. 11 may be animated will be apparent to those of ordinary skill in the art in view of the teachings herein.

In some versions, the virtual endoscopic view of FIG. 11 is shown adjacent to a real endoscopic view of the same anatomical structures, such that the physician (54) may view both images together and move the actual guide catheter in a way such that the real endoscopic view matches the virtual endoscopic view. In versions where the endoscope and includes a sensing coil (100) or other sensor, the virtual endoscopic view may be updated in real time to ensure that the line of sight for the virtual endoscopic view matches (or at least closely approximates) the line of sight for the real endoscopic view.

In versions where the guide catheter and/or guidewire includes a sensing coil (100) or other sensor, the virtual endoscopic view of FIG. 11 may further include a superimposed graphical representation of the real guide catheter and/or the real guidewire. These superimposed graphical representations may be updated in real time. This may enable the physician (54) to directly correlate the actual positioning of the real guide catheter with graphical representation (800); and the actual positioning of the real guidewire with graphical representation (810). The physician (54) may thus move the real guide catheter and guidewire until the superimposed representations of the real guide catheter and guidewire overlap the corresponding graphical representations (800, 810). In some such versions, the superimposed graphical representation of the real guide catheter and the real guidewire are provided in semi-transparent form; while graphical representations (800, 810) are provided in opaque form. In some other versions, the superimposed graphical representation of the real guide catheter and the real guidewire are provided in opaque form; while graphical representations (800, 810) are provided in semi-transparent form. Other suitable ways in which the actual positioning of one or more instruments may be displayed in real time in the same view as intended positioning of the one or more instruments will be apparent to those of ordinary skill in the art in view of the teachings herein. In some versions where system (20) is tracking the positioning and movement of one or more of the instruments during the surgical procedure, system (20) may provide an audible alert and/or a visual alert to the physician (54) to indicate when the physician (54) has unacceptably deviated from the operation plan or instructions. System (20) may also provide further instructions on what the physician (54) must do in order to get back on track with the operation plan.

As another merely illustrative variation of the view shown in FIG. 11, the view may be provided as an enhanced, real endoscopic image. For instance, view may include a real depiction of the guide catheter, but superimpose one or more arrows and/or other directional indicators on or near the real depiction of the guide catheter in order to indicate to the physician (54) how the guide catheter should be oriented and moved.

Figure 12:
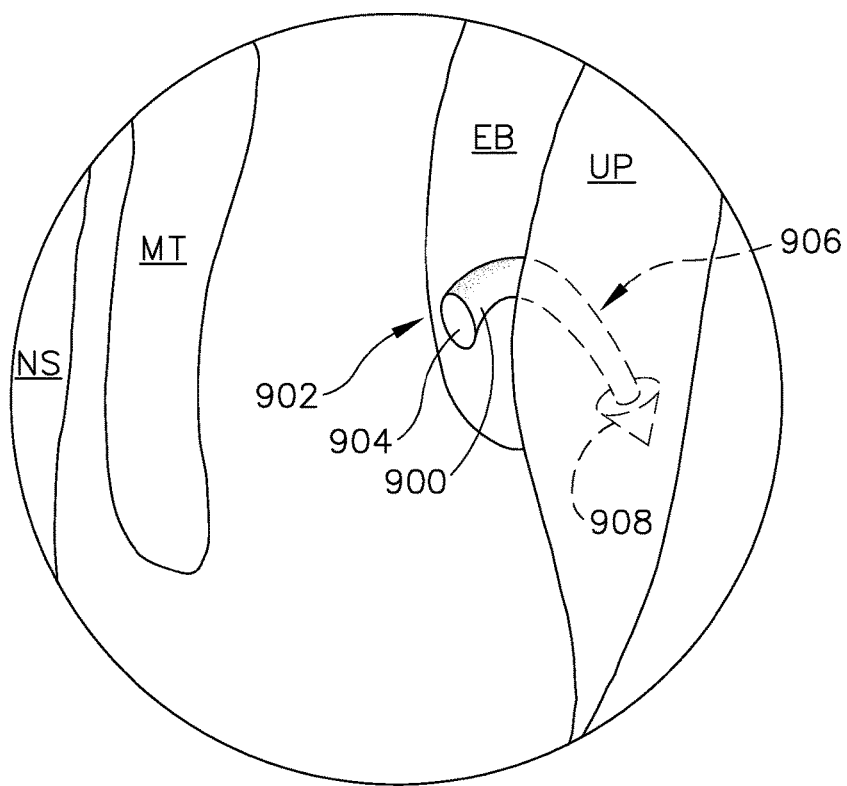
FIG. 12 depicts a virtual endoscopic view of a middle meatus of a human head, with a three-dimensional arrow, that may be that may be rendered as an instructional image in an operation plan for a surgical procedure.

FIG. 12 shows an example of another one of the instructional images that may be displayed in step (406). In particular, FIG. 12 presents a virtual endoscopic view showing a three-dimensional guide arrow (900) from the viewpoint of an endoscope whose line of sight is oriented toward the middle meatus of the patient (22). The view thus shows the position and orientation of guide arrow (900) in relation to graphical representations of the nasal septum (NS), the middle turbinate (MT), the ethmoid bulla (EB), and the uncinate process (UP).

The three-dimensional configuration of guide arrow (900) provides the physician with a sense of how the path of a guide catheter and guidewire should traverse the three-dimensional space of the middle meatus to get around the uncinate process (UP) and thereby reach the maxillary sinus ostium (MSO). In particular, guide arrow (900) includes a proximal portion (902) presenting a proximal face (904); and a distal portion (906) presenting a conical tip (908). The inclusion and configuration of face (904) and tip (908) enable arrow (900) to visually convey an instrument path through three-dimensional space more effectively than a two-dimensional arrow would be able to. In addition, since guide arrow (900) traverses the space that is lateral to uncinate process (UP), the instructional image depicts the distal end (906) of guide arrow (906) in semi-transparent form; while depicting the proximal end (902) of guide arrow (906) in opaque form. The uncinate process (UP) is depicted in opaque form in this example. In another exemplary variation, the uncinate process (UP) is depicted in semi-transparent form. In such versions, the distal end (906) of guide arrow (900) may be depicted in opaque form. Other suitable ways in which the instructional image may handle the obscuring of instrument paths by anatomical structures will be apparent to those of ordinary skill in the art in view of the teachings herein.

Figure 13A:
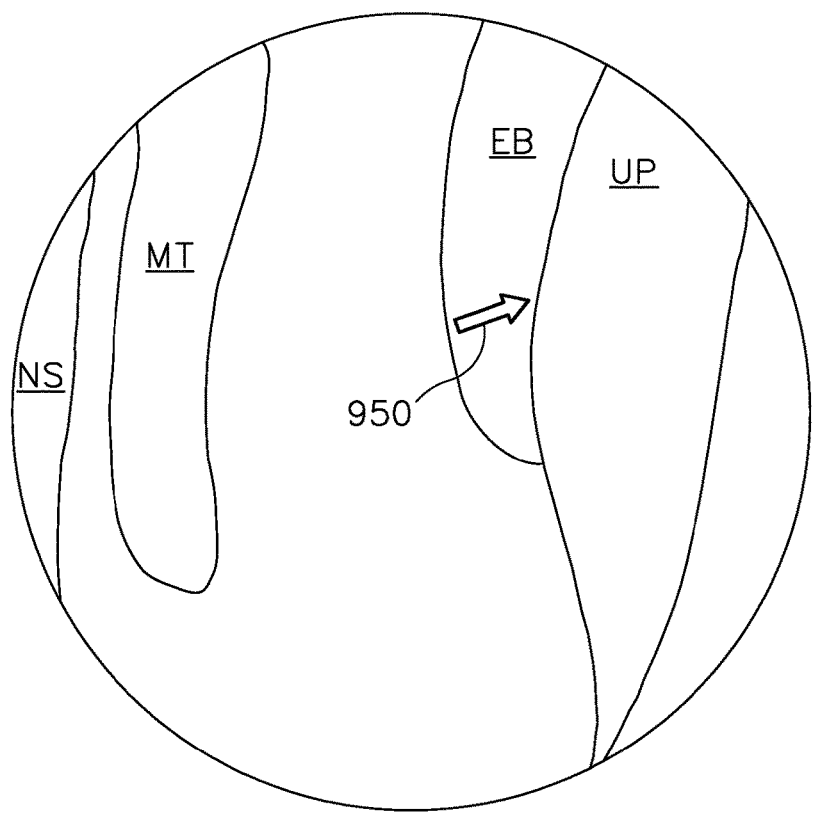
FIG. 13A depicts a virtual endoscopic view of a middle meatus of a human head, with a first arrow of an animated series, that may be that may be rendered as an instructional image in an operation plan for a surgical procedure.
Figure 13B:
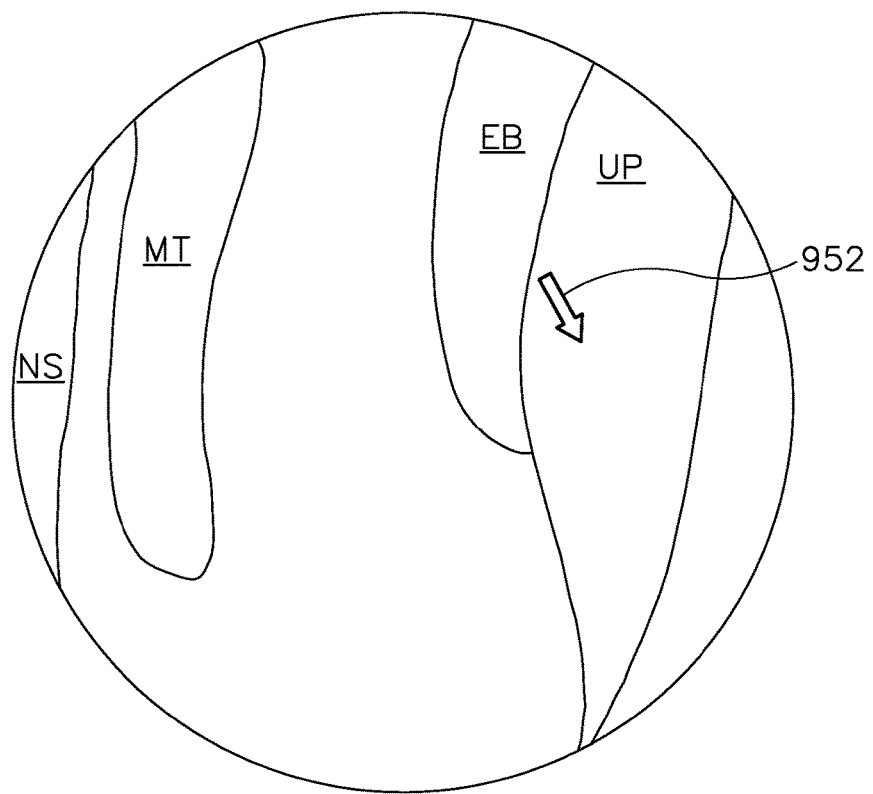
FIG. 13B depicts a virtual endoscopic view of a middle meatus of a human head, with a second arrow of an animated series, that may be that may be rendered as an instructional image in an operation plan for a surgical procedure.
Figure 13C:
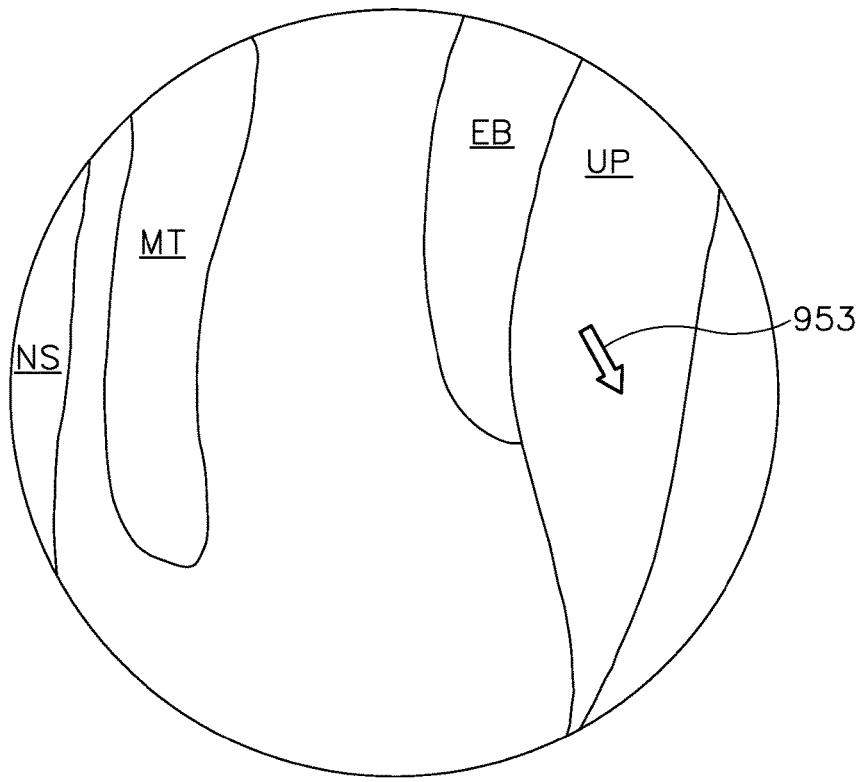
FIG. 13C depicts a virtual endoscopic view of a middle meatus of a human head, with a third arrow of an animated series, that may be that may be rendered as an instructional image in an operation plan for a surgical procedure.

FIGS. 13A-13C show a series that may be depicted through another one of the instructional images that may be displayed in step (406). In particular, FIGS. 13A-13C present a virtual endoscopic view showing an animated guide arrow (950) from the viewpoint of an endoscope whose line of sight is oriented toward the middle meatus of the patient (22). The view thus shows a moving representation of the path to be traversed by an instrument in relation to graphical representations of the nasal septum (NS), the middle turbinate (MT), the ethmoid bulla (EB), and the uncinate process (UP). It should be understood that the instructional image may repeatedly cycle through sequence of the view of FIG. 13A, then the view of FIG. 13B, then the view of FIG. 13C, such that the physician (54) may observe the movement of guide arrow (950) in order to determine the appropriate path for the instrument. As shown in FIG. 13A, guide arrow (950) is solid. However, in FIGS. 13B-13C, guide arrow (950) is not solid. This transition from solid to non-solid indicates that the path goes around the uncinate process (UP) to reach the maxillary sinus ostium (MSO). Other suitable ways in which the movement of animated guide arrow (950) behind an anatomical structure may be depicted will be apparent to those of ordinary skill in the art in view of the teachings herein.

In addition or in the alternative to the foregoing, the instructional images may include textual annotations indicating how the instrument should be moved or otherwise manipulated. In addition or in the alternative, the instructional images may include a sequence of adjacent panels showing the instrument at various stages of the procedure, such that the physician (54) may determine the appropriate path for the instrument by viewing the image panels in a succession. In addition or in the alternative, the instructional images may include animation of the instrument to show how the instrument should be moved or otherwise manipulated. As yet another merely illustrative example, screen (56) may display a listing of textual instructions next to an instructional image, with the textual instructions providing step-by-step directions to the physician (54) on where and how to manipulate the instrument in the patient (22). Still other suitable ways in which instructional images may indicate the path for the instrument to follow will be apparent to those of ordinary skill in the art in view of the teachings herein. It should also be understood that visual instructions may be substituted or supplemented with automated voice instructions generated from stored audio files, with the audio being played through a speaker, earpiece, or some other device that may be heard by the physician (54).

It should also be understood that, in addition to indicating the desired positioning, orientation, and direction of movement for the instrument being used, the instructional images may call out certain anatomical landmarks that may assist in providing a spatial context for the physician (54). For instance, the instructional images may include text and an arrow to indicate the location of the middle turbinate (MT), text and an arrow to indicate the uncinate process (UP), text and an arrow to indicate a sinus ostium or other passageway, etc. Various suitable ways in which an instructional image may visually indicate one or more anatomical landmarks will be apparent to those of ordinary skill in the art in view of the teachings herein. Similarly, various anatomical landmarks that may be useful to indicate in an instructional image will be apparent to those of ordinary skill in the art in view of the teachings herein.

In some versions, the instructional plan may identify several procedural milestones of the selected ENT procedure and rely on completion of those milestones in order to update the instructional images. For instance, for a sinuplasty procedure processor (40) may first provide one or more instructional images depicting proper placement of a guide catheter within the nasal cavity of the patient (22). Proper placement of the guide catheter may represent the completion of a first milestone, such that processor (40) may then provide a next set of instructional images depicting proper placement of a guidewire after the guide catheter has been properly placed. Proper placement of the guidewire may represent the completion of a second milestone, such that processor (40) may then provide a next set of instructional images depicting proper placement of a dilation catheter after the guidewire has been properly placed. Proper placement of the dilation catheter may represent the completion of a third milestone, such that processor (40) may then provide a next set of instructional images depicting expansion of a dilator on the dilation catheter after the dilation catheter has been properly placed. Subsequent and other milestones for a sinuplasty procedure will be apparent to those of ordinary skill in the art in view of the teachings herein. Similarly, other suitable ways in which processor

(40) may react to completion of procedural milestones within a given surgical procedure will be apparent to those of ordinary skill in the art in view of the teachings herein. Processor (40) may determine that a milestone has been completed based on positioning data from a sensing coil (100), based on input from the physician (54), and/or based on any other suitable input(s).

While several of the foregoing examples include the real-time tracking of the positioning of instrument an instrument (e.g., using one or more sensing coils (100)), it should be understood that such tracking is not required in all versions. Some versions may simply provide instructional images without performing any kind of tracking of instrument position or movement. In such versions, processor (40) may advance through a sequence of instructional images in response to input from the physician (54) (e.g., indicating completion of a milestone, etc.). Moreover, once an operation plan has been generated (e.g., per step (406) of FIGS. 7-9)), the ENT procedure may be performed without system (20) even being present. For instance, the instructional images may simply be presented via a conventional monitor or screen, using a conventional PC or other computing device.

It should be understood from the foregoing that the use of instructional images as described above may enable the physician (54) to perform an ENT procedure more safely and more efficiently. In particular, the instructional images may eliminate or minimize the need to probe the sino-nasal anatomy of the patient (22) with a wire or other probing instrument at the beginning of an ENT procedure. Eliminating or minimizing this need to probe may prevent unnecessary trauma to anatomical structures in the nasal cavity of the patient (22) and provide faster surgery.

D. Exemplary System Arrangement

Figure 14:
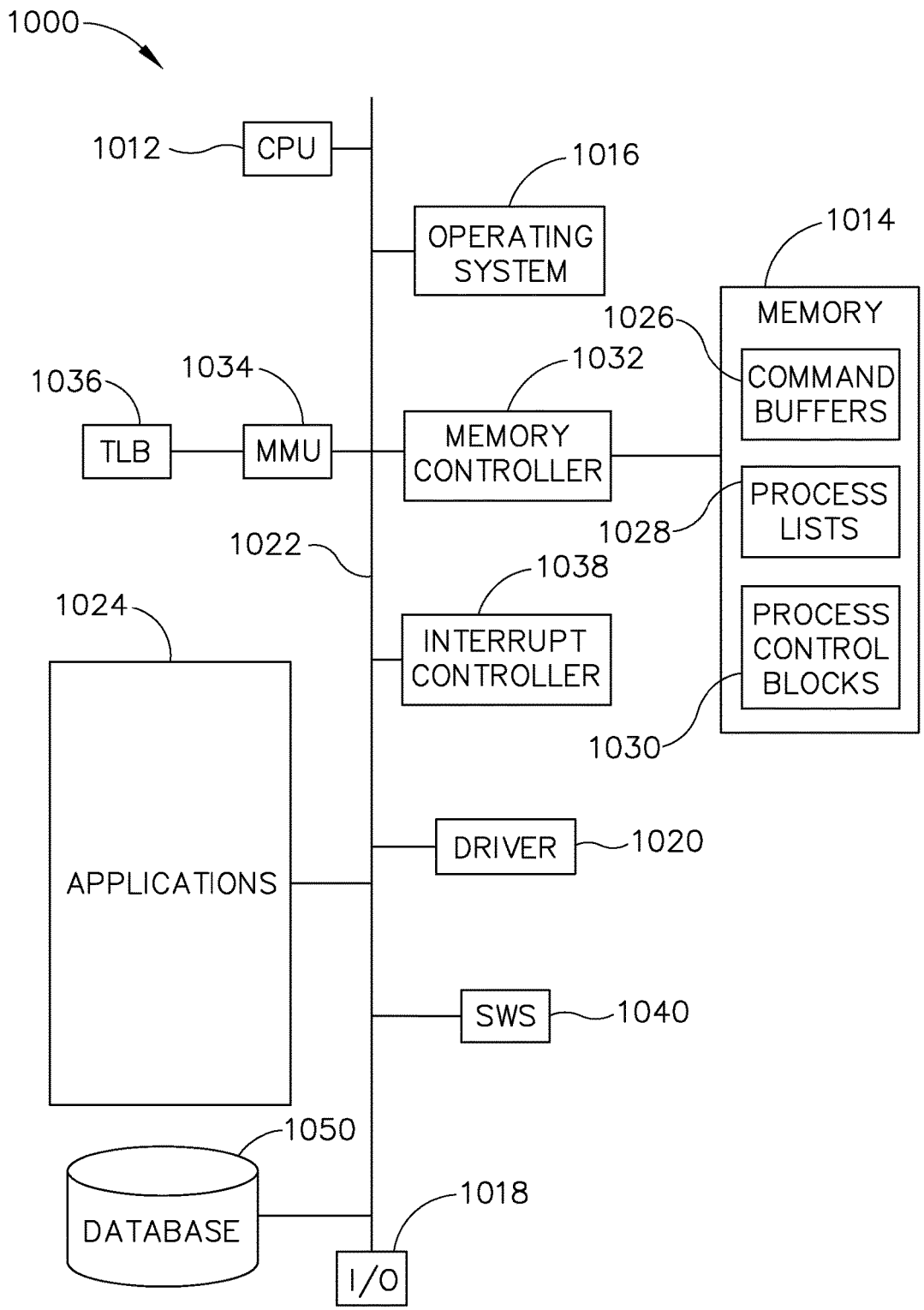
FIG. 14 depicts a schematic view of an exemplary system that may be used to provide at least a portion of the processes of FIGS. 7-9.

FIG. 14 shows components of an exemplary system (1000) that may be used to generate a surgical plan as described above and preset a series of instructional images. It should be understood that system (1000) may be integrated into console (100) shown in FIG. 1. Alternatively, system (1000) may be provided through separate hardware. As shown, system (1000) of this example comprises a central processing unit (CPU) (1012), a memory (1014), an operating system (1016), a database (1050), and a communication interface (I/O)(1018). CPU (1012) may include one or more single or multi core conventional CPUs. One or more drivers (1020) communicates with a device (not shown)) through a bus (1022) or communications subsystem to which the device connects. Such drivers may run in user mode or kernel mode. CPU (1012) executes control logic, involving operating system (1016), applications (1024), and driver (1020) to coordinate with the external hardware devices.

Memory (1014) may include command buffers (1026) that are used by CPU (1012) to send commands to other components of system (1000). Memory (1014) of this example contains process lists (1028) and other process information such as process control blocks (1030). Access to memory (1014) can be managed by a memory controller (1032), which is coupled to memory (1014). For example, memory controller (1032) may manage requests from CPU (1012) and/or from other devices for access to memory (1014).

System (1000) of the present example further includes a memory management unit (MMU) (1034), which can operate in the context of the kernel or outside the kernel in conjunction with other devices and functions for which memory management is required. MMU (1034) includes logic to perform such operations as virtual-to-physical address translation for memory page access. A translation lookaside buffer (TLB) (1036) may be provided to accelerate the memory translations. Operations of MMU (1034) and other components of system (1000) can result in interrupts produced by interrupt controller (1038). Such interrupts may be processed by interrupt handlers, for example, mediated by operating system (1016) or by a software scheduler (SWS) (1040). Of course, the foregoing components and arrangements of system (1000) are just merely illustrative examples. Other suitable components and arrangements that may be used to form system (1000) will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method comprising: (a) receiving image data, wherein the image data is associated with anatomical structures in a nasal cavity of a patient, wherein the image data is received through a computing system; (b) receiving surgical procedure data, wherein the surgical procedure data is received through a computing system; and (c) generating an operation plan, wherein the act of generating the operation plan is performed through a computing system, wherein the act of generating an operation plan comprises: (i) identifying a path for a surgical instrument in accordance with the image data and in accordance with the surgical procedure data, and (ii) generating one or more instructional images depicting the identified path for the surgical instrument in a depiction of anatomical structures in the nasal cavity of the patient.

Example 2

The method of Example 1, wherein the image data comprises data from a plurality of CT images.

Example 3

The method of any one or more of Examples 1 through 2, further comprising processing the image data to generate a three-dimensional image of anatomical structures in the nasal cavity of the patient.

Example 4

The method of any one or more of Examples 1 through 3, wherein the one or more instructional images include a three-dimensional image of anatomical structures in the nasal cavity of the patient.

Example 5

The method of Example 4, wherein the one or more instructional images further include a three-dimensional arrow indicating the identified surgical instrument path in the three-dimensional image of anatomical structures in the nasal cavity of the patient.

Example 6

The method of any one or more of Examples 1 through 5, wherein the act of receiving surgical procedure data comprises receiving input indicating selection of a surgical procedure.

Example 7

The method of Example 6, wherein the act of receiving surgical procedure data further comprises retrieving surgical data from a database in accordance with the received input indicating selection of a surgical procedure.

Example 8

The method of any one or more of Examples 1 through 7, wherein the act of receiving surgical procedure data comprises receiving a selection of a transparency level for one or more anatomical structures in the nasal cavity of the patient in at least one of the one or more instructional images.

Example 9

The method of any one or more of Examples 1 through 8, wherein the act of receiving surgical procedure data comprises receiving a selection of a field of view to be depicted in at least one of the one or more instructional images.

Example 10

The method of any one or more of Examples 1 through 8, wherein the act of receiving surgical procedure data comprises receiving input indicating a path for a surgical instrument relative to one or more anatomical structures in the nasal cavity of the patient.

Example 11

The method of any one or more of Examples 1 through 10, further comprising applying a sino-nasal structure recognition algorithm to the received image data.

Example 12

The method of any one or more of Examples 1 through 11, further comprising manipulating the image data to highlight an outflow tract associated with at least one paranasal sinus of the patient.

Example 13

The method of any one or more of Examples 1 through 12, further comprising: (a) receiving an endoscopic video image from an endoscope inserted into the nasal cavity of the patient; and (b) presenting the endoscopic video image while simultaneously presenting the one or more instructional images.

Example 14

The method of Example 13, wherein the one or more instructional images and the endoscopic video image are presented simultaneously through a single display screen.

Example 15

The method of Example 14, wherein the one or more instructional images and the endoscopic video image are presented simultaneously through separate image panels of the same display screen.

Example 16

The method of Example 13, wherein the act of presenting the endoscopic video image while simultaneously presenting the one or more instructional images comprises superimposing an instrument path indicator on the endoscopic video image.

Example 17

The method of any one or more of Examples 1 through 16, further comprising: (a) receiving position data from a position sensor of a surgical instrument; and (b) incorporating the position data into the one or more instructional images to depict actual positioning of the surgical instrument in relation to planned positioning of the surgical instrument, wherein the planned positioning of the surgical instrument is based on the identified path.

Example 18

The method of any one or more of Examples 1 through 17, wherein at least one of the one or more instructional images comprises a video image.

Example 19

A method comprising: (a) receiving image data, wherein the image data is associated with anatomical structures in a nasal cavity of a patient, wherein the image data is received through a computing system; (b) receiving surgical procedure data, wherein the surgical procedure data is received through a computing system; and (c) generating at least one instructional image identifying a path for a surgical instrument in accordance with the image data and in accordance with the surgical procedure data, wherein the act of generating the at least one instructional image is performed through a computing system; wherein the at least one instructional image includes a representation of a surgical instrument positioned and oriented in accordance with the identified path in a depiction of anatomical structures in the nasal cavity of the patient.

Example 20

A method comprising: (a) receiving image data, wherein the image data is associated with anatomical structures in a nasal cavity of a patient, wherein the image data is received through a computing system; (b) receiving surgical procedure data, wherein the surgical procedure data is received through a computing system; and (c) generating at least one instructional image identifying a path for a surgical instrument in accordance with the image data and in accordance with the surgical procedure data, wherein the act of generating the at least one instructional image is performed through a computing system; wherein the at least one instructional image shows a moving representation of a surgical instrument along the identified path in a depiction of anatomical structures in the nasal cavity of the patient.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method comprising:
   (a) receiving image data, wherein the image data is associated with anatomical structures in a nasal cavity of a patient, wherein the image data is received by a computing system;
   (b) receiving surgical procedure data, wherein the surgical procedure data is received by the computing system, based upon a user selecting a nasal passageway, and the computing system automatically accessing a set of sinuplasty procedure data for the nasal passageway;
   (c) generating an operation plan, wherein the act of generating the operation plan is performed by the computing system, wherein the act of generating the operation plan comprises:
      (i) identifying a path for a surgical instrument in accordance with the image data and in accordance with the surgical procedure data, wherein the surgical instrument comprises a guidewire,
      (ii) generating a set of instructional images depicting the identified path for the surgical instrument in a depiction of the anatomical structures in the nasal cavity of the patient;
      (iii) automatically identifying at least two anatomical structures in accordance with the image data using a sino-nasal recognition algorithm;
      (iv) setting a color for a first anatomical structure of the at least two anatomical structures based upon a user color input; and
      (v) setting a transparency for a second anatomical structure of the at least two anatomical structures based upon a user transparency input, wherein the transparency input indicates a level of opacity less than 100%;
   (d) during the execution of the operation plan, receiving an endoscopic video image from an endoscope inserted into the nasal cavity of the patient;

(e) while the surgical instrument is being used, receiving, at the computing system, position data from a sensing coil located at a distal tip of the guidewire of the surgical instrument;
(f) presenting the endoscopic video image while simultaneously presenting the set of instructional images; and
(g) executing the operation plan using the endoscopic video image and the set of instructional images;
wherein the act of presenting the endoscopic video image while simultaneously presenting the set of instructional images comprises:
  (i) superimposing an instrument path indicator on the endoscopic video image, wherein at least one part of the instrument path is opaque to indicate that it is directly visible and at least one other part of the instrument path is semi-transparent to indicate that it is not directly visible,
  (ii) incorporating the position data into the set of instructional images to depict a graphical representation of the surgical instrument's actual position in relation to the instrument path indicator,
  (iii) displaying a first image from the set of instructional images that is associated with a first stage of a procedure based upon the position data indicating the first stage of the procedure is being performed,
  (iv) superimposing a set of directional indicators on the graphical representation, wherein the set of directional indicators shows a change in position and a change in orientation that must be made with the surgical instrument in order to align the graphical representation with the instrument path indicator; and
  (v) displaying a second image from the set of instructional images that is associated with a second stage of the procedure based upon the position data indicating that the second stage of the procedure is being performed.

2. The method of claim 1, wherein the image data comprises data from a plurality of computed tomography (CT) images.

3. The method of claim 1, wherein the act of receiving surgical procedure data comprises receiving a selection of a field of view to be depicted in at least one of the set of instructional images.

4. The method of claim 1, wherein the act of receiving surgical procedure data comprises receiving input indicating a path for a surgical instrument relative to one or more anatomical structures in the nasal cavity of the patient.

5. The method of claim 1, further comprising manipulating the image data to highlight an outflow tract associated with at least one paranasal sinus of the patient.

6. The method of claim 1, wherein at least one of the set of instructional images comprises a video image.

7. The method of claim 1, wherein the computing system comprises a sinus surgery system in communication with at least one other computing device over a network, wherein the sinus surgery system is operable to perform image guided surgery.

8. A method comprising:
(a) receiving image data, wherein the image data is associated with anatomical structures in a nasal cavity of a patient, wherein the image data is received by a computing system;
(b) receiving surgical procedure data, wherein the surgical procedure data is received by the computing system;
(c) generating a set of instructional images identifying a path for a surgical instrument in accordance with the image data and in accordance with the surgical procedure data, wherein the act of generating the set of instructional images is performed by the computing system;
(d) for each stage of a surgical procedure associated with the set of instructional images, determining a current stage of the surgical procedure based upon position data from a position sensor located at a distal tip of the surgical instrument;
(e) based upon the current stage of the surgical procedure, displaying an instructional image of the set of instructional images that is associated with the current stage of the surgical procedure; and
(f) during the surgical procedure, providing an alert to a physician when position data from the position sensor indicates that the surgical instrument has deviated from the identified path;
wherein generating the set of instructional images comprises:
  (i) analyzing the image data and automatically identifying a set of outflow tracts of the paranasal sinuses of the patient; and
  (ii) adding a color highlight to the set of outflow tracts;
wherein the displayed instructional image includes:
  (i) a representation of a surgical instrument destination positioned and oriented in accordance with the identified path in a depiction of the anatomical structures in the nasal cavity of the patient, wherein the representation of the surgical instrument destination is a semi-transparent image of the surgical instrument;
  (ii) a graphical representation of an actual surgical instrument positioned and oriented in accordance with the position data, wherein the graphical representation of the actual surgical instrument position is an opaque image of the surgical instrument; and
  (iii) the alert, wherein the alert is a set of directional indicators superimposed on the graphical representation, wherein the set of directional indicators shows a change in position and a change in orientation that must be made with the surgical instrument in order to align the graphical representation with the identified path.

* * * * *